(12) United States Patent      (10) Patent No.: US 9,751,758 B2
Gang et al.      (45) Date of Patent: Sep. 5, 2017

(54) RATIONAL ASSEMBLY OF NANOPARTICLE SUPERLATTICES WITH DESIGNED LATTICE SYMMETRIES

(71) Applicant: BROOKHAVEN SCIENCE ASSOCIATES, LLC, Upton, NY (US)

(72) Inventors: Oleg Gang, New York, NY (US); Fang Lu, Miller Place, NY (US); Miho Tagawa, Nagoya (JP)

(73) Assignee: Brookhaven Science Associates, LLC, Upton, NY (US)

( * ) Notice: Subject to any disclaimer, the term of this patent is extended or adjusted under 35 U.S.C. 154(b) by 73 days.

(21) Appl. No.: 14/373,161

(22) PCT Filed: Jan. 18, 2013

(86) PCT No.: PCT/US2013/022133
§ 371 (c)(1),
(2) Date: Jul. 18, 2014

(87) PCT Pub. No.: WO2013/109880
PCT Pub. Date: Jul. 25, 2013

(65) Prior Publication Data
US 2015/0017444 A1    Jan. 15, 2015

Related U.S. Application Data

(60) Provisional application No. 61/587,786, filed on Jan. 18, 2012.

(51) Int. Cl.
*C07H 21/04*      (2006.01)
*B82B 3/00*      (2006.01)
(Continued)

(52) U.S. Cl.
CPC .................. *B82B 3/00* (2013.01); *C12Q 1/68* (2013.01); *B82Y 30/00* (2013.01); *B82Y 40/00* (2013.01);
(Continued)

(58) Field of Classification Search
None
See application file for complete search history.

(56) References Cited

U.S. PATENT DOCUMENTS 5,637,508 A    6/1997   Kidwell et al.
2005/0130167 A1    6/2005   Bao et al.
(Continued)

OTHER PUBLICATIONS

International Search Report of International Application PCT/US2013/022133—Date mailed: Mar. 15, 2013, 4 pages.
(Continued)

*Primary Examiner* — Alexandre Ferre
(74) *Attorney, Agent, or Firm* — Dorene M. Price; Lars O. Husebo

(57) ABSTRACT

A method for lattice design via multivalent linkers (LDML) is disclosed that introduces a rationally designed symmetry of connections between particles in order to achieve control over the morphology of their assembly. The method affords the inclusion of different programmable interactions within one linker that allow an assembly of different types of particles. The designed symmetry of connections is preferably provided utilizing DNA encoding. The linkers may include fabricated "patchy" particles, DNA scaffold constructs and Y-shaped DNA linkers, anisotropic particles, which are preferably functionalized with DNA, multimeric protein-DNA complexes, and particles with finite numbers of DNA linkers.

16 Claims, 10 Drawing Sheets

Library of Symmetric Linkers

DNA constructs

Anisotropic particles

Multimeric protein-DNA constructs

"Patchy" particles

(51) Int. Cl.
 C12Q 1/68 (2006.01)
 B82Y 30/00 (2011.01)
 B82Y 40/00 (2011.01)
(52) U.S. Cl.
 CPC ........ Y10S 977/84 (2013.01); Y10T 428/2982 (2015.01)

(56) References Cited

U.S. PATENT DOCUMENTS

2009/0258355 A1 10/2009 Maye et al.
2009/0275465 A1* 11/2009 Gang .................. C12Q 1/6816
 502/159

OTHER PUBLICATIONS

Written Opinion of the International Searching Authority of International Application PCT/US2013/022133—Date mailed: Mar. 15, 2013, 4 pages.
Final Office Action, U.S. Appl. No. 14/111,732, dated: Apr. 27, 2015, 10 pages.
Jones, M., et al., "DNA-nanoparticle superlattices formed from anisotropic building blocks," Nature Materials, vol. 9, pp. 913-917, 2010 and Supplementary Information, 44 pages [online] [retrieved Sep. 9, 2015] from the Internet <URL: http://www.nature.com/mnat/journal/v9/n11/abs/nrnat2870.html>.
Glotzer, S., et al., "Anisotropy of building blocks and their assembly into complex structures," Nature Materials, vol. 6, pp. 57-562, (2007).
Mastroianni, A., et al., "Pyramid and Chiral Groupings of Gold Nanocrystals Assembled Using DNA Scaffolds," Journal of the American and Chemical Society, vol. 131, pp. 8455 to 8459, (2009).
MacFarlane, R., et al., "Nanoparticle Superlattice Engineering with DNA," Science, vol. 334, pp. 204-208, (2011).
Mirkin, C., et al., "A DNA-based method for rationally assembling nanoparticles into macroscopic materials," Nature, vol. 382, pp. 607-609, (1996).
Nykypanchuk, D., et al., "DNA-guided crystallization of colloidal nanoparticles," Nature, vol. 451, pp. 549-552, (2008).
Zhang, Z., et al., "Self-Assembly of Patchy Particles into Diamond Structures through Molecular Mimicry," Langmuir, vol. 21, No. 25, pp. 11547 to 11551, (2005).
MacFarlane, R., et al., "Colloidal Assembly via Shape Complementarity," ChemPhysChem, vol. 11, pp. 3115 to 3217, (2010).
Starr, F., et al., "Model for assembly and gelation of four-armed DNA dendrimers," Journal of Physics: Condensed Matter, vol. 18, pp. L347 to L353, (2006).
Lo, P., et al., "Self-assembly of three-dimensional DNA nanostructures and potential biological applications," Current Opinion in Chemical Biology, vol. 14, pp. 597-607, (2010).
Yang, H., et al., "DNA modified with metal complexes: Applications in the construction of higher order metal-DNA nanostructures," Coordination Chemistry Reviews, vol. 254, pp. 2403 to 2415, (2010).
Goodman, R., et al., "Reconfigurable, braced, three-dimensional DNA nanostructures," Nature Nanotechnology, vol. 3, pp. 93-96, (2008).
Lin, C., et al., "Designer DNA Nanoarchitectures," Biochemistry, vol. 48, No. 8, pp. 1663 to 1674, (2009).
Zhang, C., et al., "Symmetry Controls the Face Geometry of DNA Polyhedra," Journal of the American Chemical Society, vol. 131, pp. 1413 to 1415, (2009).
Busbee, B., et al., "An Improved Synthesis of High-Aspect-Ratio Gold Nanorods," Advanced Materials, vol. 15, No. 5, pp. 414-416, (2003).
Chen, S., et al., "Silver Nanodisks: Synthesis, Characterization and Self-Assembly," The Journal of Physical Chemistry B, vol. 106, No. 42, pp. 10777 to 10781, (2002).

Chen, S., et al., "Synthesis and Characterization of Truncated Triangular Silver Nanoplates," Nano Letters, vol. 2, No. 9, pp. 1003 to 1007, (2002).
Lee, S., et al., "Single-Crystalline Star-Shaped nanocrystals and Their Evolution: Programming the Geometry of Nano-Building Blocks," Journal of the American Chemical Society, vol. 124, pp. 11244 to 11245, (2002).
Chen, S., et al., "Monopod, Bipod, Tripod and Tetrapod Gold Nanocrystals," Journal of the American Chemical Society, vol. 125, pp. 16186 to 16187, (2003).
Sun, Y., et al., "Shape-Controlled Synthesis of Gold and Silver Nanoparticles," Science, vol. 298, pp. 2176 to 2179, (2002).
Ahmadi, T.,.et al., "Shape-Controlled Synthesis of Colloidal Platinum Nanoparticles," Science, vol. 272, pp. 1924 to 1926, (1996).
Oldenburg, S., et al., "Infrared extinction properties of gold nanoshells," Applied Physics Letters, vol. 75, No. 19, pp. 2897 to 2899, (1999).
Park, S., et al., "Synthesis and Magnetic Studies of Uniform Iron Nanorods and Nanospheres," Journal of the American Chemical Society, vol. 122, pp. 8581 to 8582, (2000).
Hao, E., et al., "Synthesis of Silver Nanodisks Using Polystyrene Mesospheres as Templates," Journal of the American Chemical Society, vol. 124, pp. 15182 to 15183, (2002).
Hao, E., et al., "Synthesis and Optical Properties of 'Branched' Gold Nanocrystals," Nano Letters, vol. 4, No. 2, pp. 327-330, (2004).
Hao, E., et al., "Optical Properties of Metal Nanoshells," Journal of Physical Chemistry B, vol. 108, pp. 1224 to 1229, (2004) and Supplementary Information, 3 pages [online] [retrieved Sep. 1, 2015] from the Internet <URL: http://pubs.acs.org/doi/pdf/10.1021/jp036301n >.
Maye, M., et al., "Adenovirus Knob Trimmers as Tailorable Scaffolds for Nanoscale Assembly," Small, vol. 4, No. 11, pp. 1941 to 1944, (2008).
Manoharan, V., et al., "Dense Packing of Symmetry in Small Clusters of Microspheres," Science, vol. 301, pp. 483-487, (2003) and Supporting Material, pp. 1-3 [online] [retrieved Sep. 9, 2015] from the Internet <URL: http://www.sciencemag.org/content/301/5632/483 >.
Niu, W., et al., "Selective Synthesis of Single-Crystalline Rhombic Dodecahedral, Octahedral and Cubic Gold Nanocrystals," Journal of the American Chemical Society, vol. 131, pp. 697-703, (2009) and Supporting Information, pp. S1-S3 [online] [retrieved Sep. 9, 2015] from the Internet <URL: http://pubs.acs.org/doi/pdf/10.1021/ja804115r >.
Lu, F., et al., "Truncated Ditetragonal Gold Prisms as Nanofacet Activators of Catalytic Platinum," Journal of the American Chemical Society, vol. 133, pp. 18074 to 18077, (2011) and Supporting Information, pp. S1-S6 [online] [retrieved Sep. 9, 2015] from the Internet <URL: http://pubs.acs.org/doi/pdf/10.1021/ja207848e >.
Vial, S>, et al., "Plasmon Coupling in Layer-by-Layer Assembled Gold Nanorod Films," Langmuir, vol. 23, pp. 4606 to 4611, (2007) and Supporting Information, 4 pages [online] [retrieved Sep. 9, 2015] from the Internet <URL: http://pubs.acs.org/doi/pdf/10.1021/1a063753t >.
Mirkin, C., et al., "A DNA-based method for rationally assembling nanoparticles into macroscopic materials," Nature, vol. 382(6592), pp. 607-609, (1996).
Alivisatos, A. et al., "Organization of 'nanocrystal molecules' using DNA," Nature, vol. 382(6592), pp. 609-611, (1996).
D. Nykypanchuk, D., et al., "DNA-guided crystallization of colloidal nanoparticles," Nature, vol. 451(7178), pp. 549-552, (2008).
Park, S. et al., "DNA-programmable nanoparticle crystallization," Nature, 451(7178), pp. 553-556, (2008).
Xiong, H., et al., "Phase Behavior of Nanoparticles Assembled by DNA Linkers," Physical Review Letters, 102(1), pp. 015504-(1-4), (2009).
MacFarlane, R., et al., "Establishing the Design Rules for DNA-Mediated Colloidal Crystallization," Angewandte Chemie-International Edition, vol. 122, pp. 4693 to 4696, (2010).
Jones, M., et al., "DNA-nanoparticle superlattices formed from anisotropic building blocks," Nature Materials, vol. 9(11), pp. 913-917, (2010).

(56) References Cited

OTHER PUBLICATIONS

Lee, J., et al., "Silver nanoparticle-oligonucleotide conjugates based on DNA with triple cyclic disulfide moieties," Nano Letters, vol. 7(7): p. 2112-2115, (2007).
Pal, S., et al., "Stable silver nanoparticle-DNA conjugates for directed self-assembly of core-satellite silver-gold nanoclusters," *Chemical Communications*, vol. (40), pp. 6059-6061, (2009).
Maye, M. et al., "Photoluminescence enhancement in CdSe/Zns-DNA linked-Au nanoparticle heterodimers probed by single molecule spectroscopy," *Chemical Communications*, vol. 46(33), pp. 6111-6113, (2010).
Hiliard, L., et al., "Immobilization of oligonucleotides onto silica nanoparticles for DNA hybridization studies," *Analytica Chimica Acta*, vol. 470(1), pp. 51-56, (2002).
Cutler, J., et al., "Polyvalent Oligonucleotide Iron Oxide Nanoparticle "Click" Conjugates," *Nano Letters*, vol. 10(4), pp. 1477-1480, (2010).
Lee, C., et al., "Conjugation of $\gamma$-$Fe_2O_3$ nanoparticles with single strand oligonucleotides," *Journal of Magnetism and Magnetic Materials*, vol. 304(1), pp. e412-e414, (2006).
Murray, C., et al., "Synthesis and Characterization of Nearly Monodisperse Cde (E=S, Se, Te) Semiconductor Nanocrystallites," *Journal of the American Chemical Society*, vol. 115(19), pp. 8706-8715, (1993).
Dabbousi, B., et al. "(CdSe)ZnS core-shell quantum dots: Synthesis and characterization of a size series of highly luminescent nanocrystallites," *Journal of Physical Chemistry B*, vol. 101(46), pp. 9463-9475, (1997).
Lim, B., et al., "Shape-Controlled Synthesis of Pd Nanocrystals in Aqueous Solutions," *Advanced Functional Materials*, vol. 19(2), pp. 189-200, (2009).
Sun, Y., et al., "Shape-controlled synthesis of gold and silver nanoparticles", Science, 2002, 298(5601): p. 2176-2179.
Medintz, I., et al., "Quantum dot bioconjugates for imagining, labelling and sensing," *Nature Materials*, vol. 4(6), pp. 435-446, (2005).
Kang, S., et al., "Quantum-dot light-emitting diodes utilizing Cd Se/Zn S nanocrystals embedded in $TiO_2$ thin film," *Applied Physics Letters*, vol. 93(19), pp. 191116-1 to 191116-3, (2008).
Pellegrino, T., et al., "Hydrophobic Nanocrystals Coated with an Amphiphilic Polymer Shell: A General Route to Water Soluble Nanocrystals," *Nano Letters*, vol. 4(4), pp. 703-707, (2004).
Cigler, P., et al., "DNA-controlled assembly of a NaT1 lattice structure from gold nanoparticles and protein nanoparticles," *Nature Materials*, vol. 9(11), pp. 918-922, (2010).
Zheng, W., et al., "Distance-Dependent Fluorescence Quenching of Conjugated Polymers on Au/Ag Striped Nanorods," *Journal of Physical Chemistry C*, vol. 114(41), pp. 17829-17835, (2010).
Hyeon, T., et al., "Synthesis of Highly Crystalline and Monodisperse Maghemite Nanocrystallites without a Size-Selection Process," *Journal of the American Chemical Society*, vol. 123(51), pp. 12798 to 12801, (2001).
Knowroski, C., et al., "Dynamics and Statics of DNA-Programmable Nanoparticle Self-Assembly and Crystallization," *Physical Review Letters*, vol., 106, pp. 1-5, (2011).
Courty, A., et al., "Vibrational coherence of self-organized silver nanocrystals in f.c.c. supra-crystals," *Nature Materials*, vol. 4(5), pp. 395-398, (2005).
Urban, J., et al., "Synergism in binary nanocrystal superlattices leads to enhanced p-type conductivity in self-assembled PbTe/Ag2Te thin films," *Nature Materials*, vol. 6(2), pp. 115-121, (2007).
Redl, F., et al., "Three-dimensional binary superlattices of magnetic nanocrystals and semiconductor quantum dots," *Nature*, vol. 423, pp. 968-971, (2003).
Shevchenko, E., et al., "Structural diversity in binary nanoparticle superlattices ," *Nature*, vol. 439, pp. 55-59, (2006).
Kalsin, A., et al., "Electrostatic Self-Assembly of Binary Nanoparticle Crystals with a Diamond-Like Lattice," *Science*, vol. 312, pp. 420-424, (2006).
Evers, W., et al., "Observation of a Ternary Nanocrystal Superlattice and Its Structural , Characterization by Electron Tomography," *Angewandte Chemie-International Edition*, vol. 48(51), pp. 9655 to 9657, (2009).
Zhang, Y., et al., "Continuous Phase Transformation in Nanocube Assemblies", *Physical Review Letters*, vol. 107, pp. 135701-1 to 135701-4, (2011).
Tkachenko, a., "Morphological diversity of DNA-colloidal self-assembly," *Physical Review Letters*, vol. 89(14), pp. 148303-1 to 148303-4, (2002).
Dai, W., et al., "Valency Dependence of Polymorphism and Polyamorphism in DNA-Functionalized Nanoparticles," *Langmuir*, vol. 26, pp. 3601 to 3608, (2010).
MacFarlane, R., et al., "Nanoparticle Superlattice Engineering with DNA," *Science*, vol. 334, pp. 204-208, 2011, [online] [retrieved May 22, 2015] from the internet <URL:http://www.sciencemag.org/content/334/6053/204.full.pdf>.
Sun, D.., et al, "Binary Heterogeneous Superlattices Assembled from Quantum Dots and Gold Nanoparticles with DNA," *Journal of the American Chemical Society*, vol. 133, pp. 5252 to 5254, (2011).
Wilson, O., et al., "Effect of Pd Nanoparticle Size on the Catalytic Hydrogenation of Allyl Alcohol," *Journal of the American Chemical Society* vol. 128, pp. 4510 to 4511, (2006).
Z. Zhang and S C. Glotzer, "Self-Assembly of Patchy Particles" Nano Letters,2004,4(8), pp. 1407-1413 (DOI: 10.1021/n10493500).
A. B. Pawar and I. Kretzschmar, "Fabrication, Assembly, and Application of Patchy Particles" Macromol. Rapid Commun. 2010, 31, pp. 150-168 (DOI: 10.1002/marc.200900614).
P. Song et al., "Patchy Particle Packing under Electric Fields" J. Am. Chem. Soc.,2015,137(8), pp. 3069-3075 (DOI:10.1021/ja5127903).
E. Duguet et al., "Patchy colloidal particles for programmed self-assembly" Comptes Rendus Chimie, 2016, 19 (1-2), pp. 173182 (DOI: 10.1016/j.crci.2015.11.013).
"Patchy particles" http://www.sklogwiki.org/SklogWiki/index.php/Patchy_particles, last accessed Nov. 21, 2016.
"Patchy particles" https://en.wikipedia.org/wiki/Patchy_particles, last accessed Nov. 21, 2016.
W. Liu et al., "Diamond family of nanoparticle superlattices" Science, 2016, 351(6273), pp. 582-586 (DOI:10.1126/science.aad2080).
Y. Tian et al., "Lattice engineering through nanoparticle-DNA frameworks" Nature Materials, 2016, Advance online publication (DOI: 10.1038/NMAT4571).

\* cited by examiner

Library of Symmetric Linkers

DNA constructs

Anisotropic particles

Multimeric protein-DNA constructs

"Patchy" particles

RATIONAL ASSEMBLY OF NANOPARTICLE SUPERLATTICES WITH DESIGNED LATTICE SYMMETRIES

CROSS-REFERENCE TO A RELATED APPLICATION

This application is a U.S. national stage application and claims the benefit under 35 U.S.C. §371 of International Application No. PCT/US2013/022133 filed on Jan. 18, 2013, which claims the benefit under 35 USC. 119(e) of U.S. Provisional Application No. 61/587,786 filed on Jan. 18, 2012, the disclosure of which is incorporated herein in its entirety.

STATEMENT OF GOVERNMENT RIGHTS

This invention was made with Government support under contract number DE-AC02-98CH10886, awarded by the U.S. Department of Energy. The Government has certain rights in the invention.

FIELD OF THE INVENTION

The present invention generally relates to the field of DNA-guided particle assembly. More particularly, the present invention relates to controlling the morphology of superlattice assembly with rationally designed lattice symmetries of connections between particles.

BACKGROUND

The ability to assemble nano-objects in rationally designed 3D superlattices can open tremendous opportunities for the fabrication of new classes of materials. However, such lattices are often difficult to predict and control and are dependent on a large number of factors. (Macfarlane R. J. et al. *Science* 334, 204-208, 2011, incorporated herein by reference in its entirety). For instance, for ionic solids, Pauling developed rules that explain the relative stabilities of different lattices of simple salts, but these rules do not allow for structure control because parameters such as size and charge of atoms (and small molecules) are not tunable (L. Pauling, *The Nature of the Chemical Bond*, Cornell Univ. Press, Ithaca, N.Y., ed. 3, 1960). In fact, changing an atom's size or charge inherently changes the electronic properties that affect relative lattice stability.

In contrast, nanoparticle-based superlattice materials should allow for more control over the types of crystal lattice that they adopt, given that one can tune multiple variables, such as nanoparticle size or the presence of different organic molecule layers on the nanoparticle surface, to control superlattice stability (C. A. Mirkin, et al. *Nature* 382, 607, 1996, incorporated herein by reference in its entirety). However, predictable architectural control still remains an elusive goal, regardless of the type of particle interconnect strategy chosen (see FIG. 1): electrostatic forces, covalent and noncovalent molecular interactions, and biologically driven assembly strategies (Nykypanchuk D, et al. *Nature* 451(7178), 549-52, 2008, incorporated herein by reference in its entirety).

A conceptually simple idea for overcoming this problem is the use of "encodable" interactions between building blocks. This can in theory be directly implemented using strategies based on DNA programmability to control the placement of nanoparticles in one and two dimensions as shown in FIG. 2. For example, U.S. Pat. Pub. No. 2009/0275465 to Gang et al. (incorporated herein by reference in its entirety) discloses the formation of three-dimensional crystalline assemblies of gold nanoparticles mediated by interactions between complementary DNA molecules attached to the nanoparticles' surface. The structure has the body-centered-cubic lattice structure, which is structurally open, with particles occupying only approximately 4% of the unit cell volume. Building on this development, U.S. Pat. Pub. No. 2009/0258355 to Maye et al. (incorporated herein by reference in its entirety) discloses a method of making three-dimensional crystalline assemblies or nanoclusters using anchoring biomolecules. These systems, however, entropically favor random geometry of connections during structure formation (see FIG. 3). Thus, it becomes difficult, if not impossible, to direct a desired lattice formation.

Recently much attention was focused on theoretical studies of patchy particles (Zhang et al. *Langmuir* 21(25) 11547-11551, 2005; incorporated herein by reference in its entirety) and shape directed assembly (Macfarlane, R. J. et al. *Chemphyschem* 11(15), 3215-3217, 2010; incorporated herein by reference in its entirety). These studies focused on the number and location of sites on spherical particles, which provide attractive interactions that determine many phenomena related to the complex structure formation in liquids, solids and gels (Starr, F. W. et al. *Journal of Physics-Condensed Matter*, 2006. 18(26): p. L347-L353; incorporated herein by reference in its entirety). Interestingly, the simple early models of colloidal patchy particles were found to correlate well with findings for atomic and molecular systems. For example, in a seminal work by Kolafa and Nezdeda, a water structure was captured by a model with tetrahedral connections. (Kolafa, J. and I. Nezbeda, *Molecular Physics,* 1987. 61(1): p. 161-175; incorporated herein by reference in its entirety). Formation of networks in silica was also explained using this approach by assuming low coordination and strong bond associations. Moreover, even the dynamics were successfully modeled, including the diffusion process, and interplay between a packing driven arrest, glass transition, bond-driven arrest, and gelation. A demonstrated high degree of similarity between basic models, described by coarse modeling and experimental observation in complex molecular systems, is indicative for an important role that directionality and geometry of connection plays in structure determination.

Therefore, it would be desirable to provide a solution, which overcomes the above-described inadequacies and shortcomings in the design and synthesis of the controlled crystal nanoparticle superlattices.

SUMMARY

Recognizing the challenges of fully exploiting nanoparticle superlattices, in one embodiment, a method for lattice design via multivalent linkers (LDML) is disclosed that introduces a rationally designed symmetry of connections between particles in order to achieve control over the morphology of their assembly. Preferably, the method affords the inclusion of different programmable interactions within one particle or one linker, called "colored" interactions, that allows an assembly of different types of particles. In one exemplary embodiment, the designed symmetry of connections is provided utilizing DNA encoding.

The linkers are not particularly limited as long as they provide symmetric interactions and have multiple attachment points that, in turn, determine the phase of the 2D or 3D structures. For example, the linkers include, but not limited to, fabricated "patchy" particles, DNA scaffold constructs and Y-shaped DNA linkers, anisotropic particles, which are preferably functionalized with DNA, multimeric protein-DNA complexes (e.g., knob adenovirus and streptavidin tetramer), and particles with finite numbers (from 1 to 8) of DNA linkers. Such linkers can possess a unique symmetry that results in a desired conformation of the formed lattice and is analogous to atomic bonds. For instance, the linkers can be rods, disks, triangular prisms, multipods, cubes, octahedra, tetrahedra, hexahedra, dodecahedra, and nanoshells. By introducing linkers with a specific architecture of connecting sites the correspondence between the linker symmetry and packing of particles into superstructures is established during the self-assembly process. Thus, the LDML method allows for a rational fabrication of 2D and/or 3D structures via establishing a local connection of particles with specifically designed linkers. The successful realization of the LDML method in using nanoscale multivalent linkers with well-defined symmetry allows for rational design fabrication of superlattices from any type of particles, including spherical and quasi-spherical.

The objectives, features and advantages of the disclosed invention will be apparent from the following detailed description, which is to be read in conjunction with the accompanying drawings. The scope of the invention will be pointed out in the claims. The following drawings, taken in conjunction with the subsequent description, are presented to enable one of ordinary skill in the art to make and use the invention and to incorporate it in the context of particular applications.

BRIEF DESCRIPTION OF THE DRAWINGS

FIG. 6E is a plot obtained by small angle x-ray scattering (SAXS) of the assembly in FIGS. 6B-6D. The plot reveals the assembly lines and indexing with simple cubic model.

DETAILED DESCRIPTION

Figure 1:
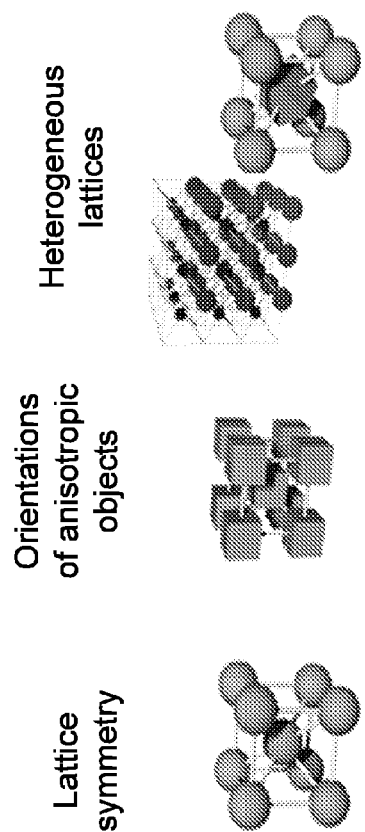
FIG. 1 shows three models of homogeneous/heterogeneous lattice assembly.
Figure 2:
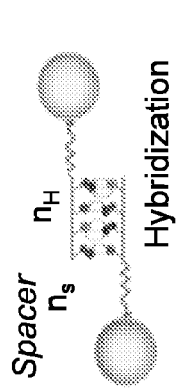
FIG. 2 illustrates hybridization of like particles using DNA.
Figure 3:
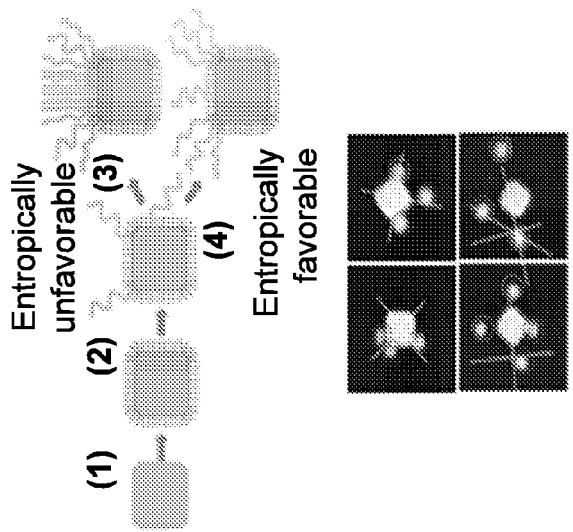
FIG. 3 illustrates lattice formation based on entropically favorable link formation between the nanoparticles.
Figure 3:
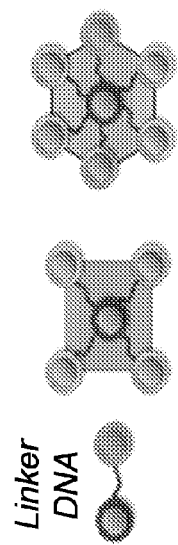

A lattice design via multivalent linkers (LDML) method introduces a rationally designed symmetry of connections between particles in order to achieve control over the morphology of their assembly. Using nanoscale multivalent linkers with specific symmetry can afford rational design of more complex, multicomponent lattices. For instance, the linkers can be rods, disks, triangular prisms, multipods, cubes, octahedra, tetrahedra, hexahedra, dodecahedra, and nanoshells. The specified symmetry of the linkers causes particles that ordinarily do not organize into a lattice or organize into one particular lattice to reorganize into a different lattice based on the symmetry of interactions afforded by the linker. For example, a tetrahedron linker can promote a spherical or quasi-spherical particle to organize into a diamond lattice instead of a body-centered cubic (BCC) lattice. Thus, a skilled artisan using LDML method can select the necessary linker to create a desired lattice with any space group described in Hahn (*International Tables for Crystallography* (2006). Vol. A: Space-group symmetry, ch. 7.1, pp. 112-717; incorporated herein by reference in its entirety). Preferably, the method affords the inclusion of different programmable interactions within one particle or one linker, called "colored" interactions, that allow an assembly of different types of particles. The interactions can be made at the facets of the linkers and/or at its vertices.

The linkers may be used in order to allow an assembly of different types of particles. The types of particles are not particularly limited, but may include nano sized particles as well as micron sized particles. Non-limiting examples include nanospheres, nanorods, nanoshells, and nanocapsules. Embodiments include the particles being made from metal, such as for example noble metals such as gold, silver, palladium, iridium, osmium, rhodium, ruthenium, or platinum. The particles may also be made from semiconductors, such as cadmium selenide, cadmium sulfide, zinc sulfide, or gallium arsenide. The particles may further also be made from oxides, such silicon dioxide ($SiO_2$) or iron oxide ($Fe(II)_3O_4$ or $Fe(III)_2O_3$). The particles may further still also be made from combinations of materials, such as for example gold coated silicon dioxide (an example of a nanoshell).

In an embodiment, the designed symmetry of connections is provided to assemble spherical particles. The spherical particles may have diameters ranging from about 1 nm to about 1 µm or more. All individual values and subranges about 1 nm to about 1 µm or more are included herein and disclosed herein; for example, the diameters can be from a lower limit of about 1, 5, 10, 20, 27, 30, 38, 40, 44, 50, 60, 75, 80, 90 or 100 nm to an upper limit of about 25, 27, 30, 38, 40, 44, 50 60, 75, 80, 901, 100, 250, 500, 750, 800, 900, or 1,000 nm. Embodiments encompass for example spherical particles having diameters from about 5 nm to about 500, from about 10 nm to about 500, and from about 20 nm to about 60 nm.

However, nonspherical particles can also be assembled by converting nonspherical particles into quasi-spherical particles through functionalization. That is, functionalization creates a shell around any particle, thereby imitating a spherical particle (i.e. quasi-spherical).

In certain embodiments, nonspherical particles may be assembled via DNA encoding by converting the nonspherical particles into quasi-spherical particles through DNA functionalization. That is, DNA functionalization creates a shell around any particle, thereby imitating a spherical particle (i.e. quasi-spherical).

The linkers are not particularly limited in the LDML method, as long as they provide symmetric interactions and have multiple attachment points that, in turn, determine the phase of the 2D or 3D structure. Such linkers can range in size from about 1 nm to about 1 µm or more and can be composed of inorganic blocks, organic polymers, oxides (e.g. $Fe_2O_3$, $SiO_2$) and biomolecular constructs.

Figure 4A:
FIG. 4A shows four exemplary models of symmetric linkers that can be used for assembly of 2D and 3D structures whose phase is determined by the symmetry of the linker.
Figure 4A:
Figure 4A:
Figure 4A:

As illustrated in FIG. 4A, the linkers can include (1) DNA scaffold constructs, (2) anisotropic particles, (3) multimeric protein-DNA complexes, and (4) fabricated "patchy" particles. The binding between linkers and particles can be implemented in various ways known in the art. For example, U.S. Pat. Pub. No. 2009/0275465 to Gang et al. (incorporated herein by reference in its entirety) describes the formation of three-dimensional crystalline assemblies of gold nanoparticles mediated by interactions between complementary DNA molecules attached to the nanoparticles' surface. In particular, the DNA character and composition may be used to finely control the self-assembly kinetics, as well as final assembled aggregate size and morphology of superlattices.

In one embodiment, by varying the length of the complementary DNA sequence on the linker and the nanoparticle of interest, the inter-particle distance in the aggregates can be decreased or increased. In some embodiments, the complementary DNA sequence can also have a neutral, non-complementary DNA spacer sequence (flexor) that itself does not hybridize. By changing the length and the amount of neutral, non-complementary DNA relative to the aggregation-promoting complementary DNA, the sizes of the aggregates and the number of possible linkages per nanoparticle can be controlled. In this embodiment, the use of the rigidified spacer sequences provides additional enhancement of the aggregation kinetics. In some embodiments the rigidified spacer sequence comprises at least one segment of double-stranded DNA. In yet another embodiment of using DNA-induced self-assembly, the propensity for the DNA-linkages to melt at a temperature can be used for superlattice assembly. The melting (breakdown H-bonds) of DNA linkages dependents upon the sequences of DNA used, the number of linkages between nanoparticles, and the local salt environment (e.g. Mg or Na). This allows for additional lattice formation approaches to be developed based on assembly melting point, but also, the ability to simply disassemble nanoparticle assemblies. This disassembly is a useful property of these systems that can be used to modify superlattice formation by substituting a different linker nanoparticle(s).

(1) DNA Scaffold Constructs

Typically, the DNA scaffold constructs are made from 1 to 10 stands of DNA. Through Watson-Crick base pairing, a multitude of sequences can be formulated and DNA can yield self-assembling scaffolds of various conformations (i.e. cubic, tetrahedron, octahedron, etc). Although RNA and protein-based molecular self-assembly offer the structural and functional diversity, the predictability and rigidity of DNA scaffolding are advantageous for applications demanding a high degree of structural control and accuracy.

FIG. 8 show an exemplary embodiment of a DNA scaffold construct. The illustrated DNA scaffold forms a tetrahedron that allows assembly of spherical particles. In this embodiment, four single stranded (ss) DNA molecules (see Table 2; System VI) are encoded to only hybridize with each other in a specific location and orientation. As illustrated in FIG. 8A, DNA T1 has four regions of 37 base pairs (~12.3 nm) and one recognition site (Arm T1). The first T1 region hybridizes with the first T2 region. The second T1 region hybridizes with the second T4 region. The third T1 region hybridizes with the third T3 region. In contrast to the other T1 regions, the recognition site (Arm T1) hybridizes with the DNA functionalized nanoparticles (see FIG. 8C) to form DNA-nanoparticle construct. Alternatively, the nanoparticles can be covalently attached to the DNA scaffold construct by any suitable linking mechanism, for example, via biotin linker. A detailed description of synthesizing symmetric DNA scaffold constructs can be found in Lo, P. K., et al. *Current Opinion in Chemical Biology*, 2010. 14(5): p. 597-607, Yang, H. et al. *Coordination Chemistry Reviews*, 2010. 254(19-20): p. 2403-2415; Goodman, R. P., et al., *Nature Nanotechnology*, 2008. 3(2): p. 93-96; Lin, C. et al. *Biochemistry*, 2009. 48(8): p. 1663-1674; and Zhang, C., et al.,

*Journal of the American Chemical Society*, 2009. 131(4): p. 1413 (all incorporated herein by reference in their entirety).

The measurements from the small-angle x-ray scattering (SAXS) experiments (see FIG. 8B) suggest that nanoparticles with the DNA scaffold tetrahedron form superlattices having a diamond shape symmetry (see FIG. 8D), while assembly of spherical particles typically results in a body-centered cubic (BCC) lattice. Thus, by manipulating the structure and orientation of the DNA scaffold, known in the art as DNA origami, the LDML method allows rational design of complex, multicomponent lattices that include cubic, hexagonal, tetragonal, orthorhombic, etc.

(2) Anisotropic Particles

The symmetric anisotropic nanoparticle linkers that can be used in the disclosed LDML method include nanoscale rods (B. D. Busbee, et al. *Adv. Mater.* 15, 414-416, 2003; incorporated herein by reference in its entirety), disks (S. Chen, et al. *J. Phys. Chem. B* 106, 10777-10781, 2002; incorporated herein by reference in its entirety), triangular prisms (S. Chen et al. *Nano Lett.* 2, 1003-1007, 2002; incorporated herein by reference in its entirety), multipods (S.-M. Lee, et al. *J. Am. Chem. Soc.* 124, 11244-11245, 2002; S. Chen et al. *J. Am. Chem. Soc.* 125, 16186-16187, 2003; incorporated herein by reference in their entirety), cubes (Y. Sun et al. *Science* 298, 2139-2141, 2002; T. S. Ahmadi et al. *Science* 272, 1924-1926, 1996; incorporated herein by reference in their entirety), nanoshells (S. J. Oldenburg et al. *Appl. Phys. Lett.* 75, 2897-2899, 1999; incorporated herein by reference in its entirety) and other structural motifs besides cubes that belong to polyhedra, such as, but not limited to, octahedra, tetrahedra, hexahedra, dodecahedra and icosahedra.

Among the known anisotropic nanoparticles, nanorods are the most common as this structural motif is found in a broad range of materials, including CdE (E=Se, Te), Ag, Au, $TiO_2$, and others (S.-J. Park et al. *J. Am. Chem. Soc.* 122, 8581-8582, 2000; incorporated herein by reference in its entirety). However, the same materials can be used to build other structural motifs such as polyhedra (e.g. cubes), triangular prisms, nanoshells and multipods. The type and size of the material used to construct the anisotropic particles is not particularly limited and can be selected based on the desired parameters of the system. For example, the anisotropic particles can be made from metal, polymer, oxide or semiconductor and range in size between about 1 nm and about 1 μm, preferably between about 5 nm and about 500 nm or between about 500 nm and 1 μm. If the anisotropic particles are made from metal, the metal is preferably a noble metal such as gold, silver, palladium, iridium, osmium, rhodium, ruthenium, or platinum. If, however, the anisotropic particles are made from semiconductor, the semiconductor can include, but not limited to, cadmium selenide, cadmium sulfide, zinc sulfide, or gallium arsenide. If the anisotropic particles are made from oxides, the oxide can be silicon dioxide ($SiO_2$) with desired optical properties (e.g. diamond lattice) or iron oxide ($Fe(II)_3O_4$ or $Fe(III)_2O_3$) with desired plasmonic or magnetic properties.

The synthetic methods used to make the anisotropic nanoparticles have been described previously in E. Hao et al. *J. Am. Chem. Soc.* 124, 15182-15183, 2002; E. Hao, et al. *Nano Lett.* 4, 327-330, 2004; E. Hao et al. *J. Phys. Chem. B* 108, 1224-1229, 2004; all incorporated herein by reference in their entirety.

Figure 4B:
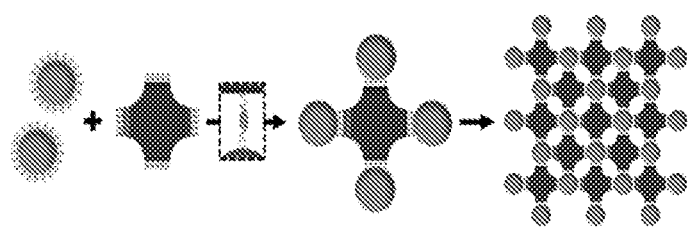
FIG. 4B illustrates the assembly of clusters and superlattice from spherical particle induced by the symmetry of a linker (cube). The binding between linker and spherical particle is encoded by DNA recognition.
Figure 4B:
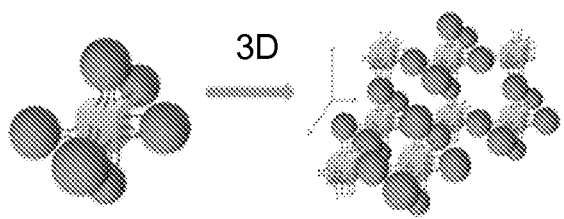
Figure 5A:
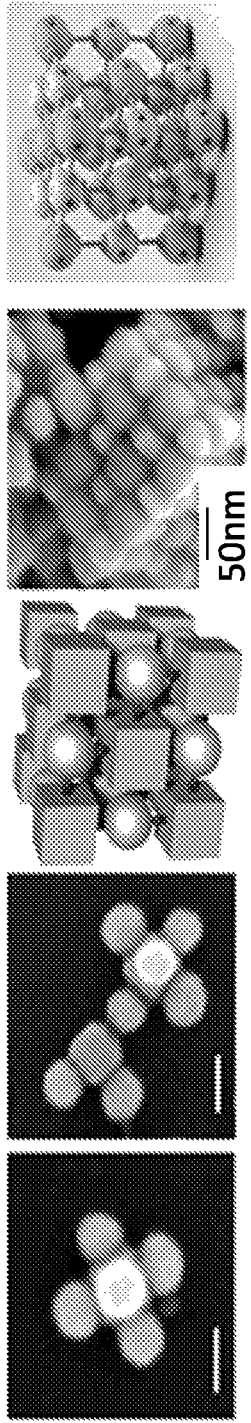
FIG. 5A shows the cube-induced assembly of spheres into a simple cubic structure (or NaCl-type structure). The first two images show the scanning electron microscope (SEM) images of the assembly of gold (Au) spheres (38 nm) around the gold (Au) cubic structure (42 nm). The third image is an idealized visualization of the formed simple cubic lattice, where spheres are organized by cubic linkers. The fourth image is the SEM of the superlattice at a resolution of 50 nm. The last image shows an atomic analog structure.
Figure 5B:
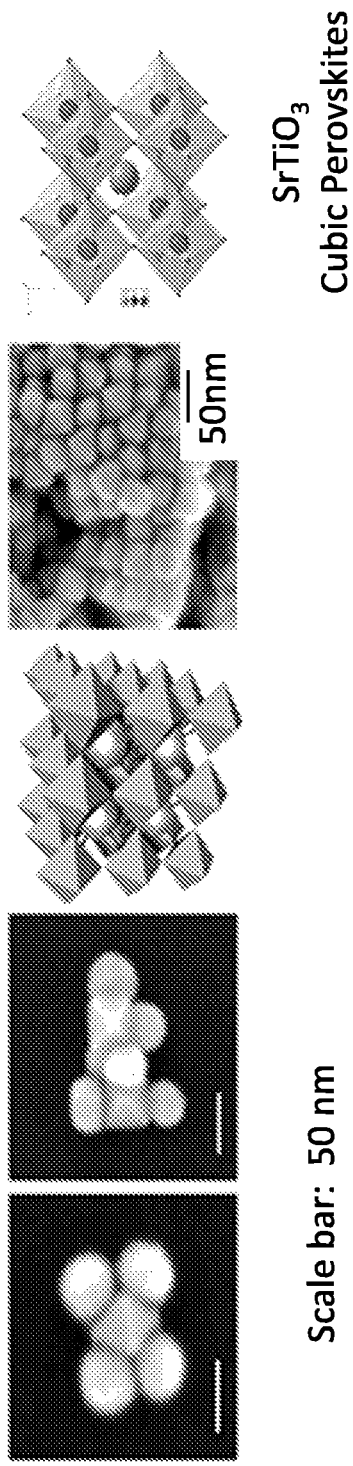
FIG. 5B shows octahedra-induced assembly of spheres and octahedral into a cubic perovskite-type structure (or SrTiO$_3$-type structure). The first two images show the SEM images of the assembly of gold (Au) spheres around the gold (Au) octahedral particle(s). The third image is an idealized visualization of the formed cubic perovskite-type lattice, where spheres are organized by an octahedral linkers. The fourth image is the SEM of the superlattice at a resolution of 50 nm. The last image shows an atomic analog structure.

To facilitate superlattice formation, the anisotropic particle linkers have connecting sites with specific symmetry due to an anisotropic nature of the linker. For example, the connecting sites of the polyhedron linker are placed at its facets. The connecting sites can provided by DNA functionalization that can hybridize with randomly placed DNA strands on the counter nanoparticle (shown as spheres in the Figures). Through Watson-Crick base pairing, the hybridization only occurs between the linker and the nanoparticle spheres. However, those skilled in the art will recognize that other methods of linking the particles can be used and the disclosed invention is not limited to only DNA hybridized connectivity. FIG. 4B illustrates an exemplary embodiment where an anisotropic particle linker with cube structural motif is hybridized with six nanoparticle spheres (one at each of its facets). The spheres, in turn, can hybridize with other anisotropic particle linkers. As shown in FIG. 5A, the cube-induced assembly of spheres results in a NaCl-type primitive cubic lattice (cP or simple cubic). Each sphere and each cube linker has six connectivity sites. FIG. 5B illustrates another example of the octahedral-induced assembly of spheres that results in perovskite-type structure observed in compounds such as $SrTiO_3$. In both cases polyhedral particles and spheres are encoded with complementary single-stranded DNA to provide mutual binding. While assembly of spherical particle typically results in a body-centered cubic (BCC) lattice, as shown in FIG. 5A the 6-fold cubic symmetry can dictate a simple cubic phase of spheres and overall NaCl-type lattice. Similarly, in the octahedra-induced assembly shown in FIG. 5B the underlying symmetry of octahedra induces a complex lattice arrangement, perovskite structure, typically exhibited by many oxides with interesting electronic and magnetic properties (general formula $ABO_3$, for example $CaTiO_3$, $SrTiO_3$).

(3) Multimeric Protein-DNA Complexes

The multimeric proteins, such as knob adenovirus and streptavidin tetramer, can be symmetrically conjugated with DNA to form linker molecules that can assist in the formation of controllable superlattices. Specifically, the introduction of structural elements with predesigned symmetries and quantized number of binding sites provides a finite and location specific connectivity sites. For instance, symmetric adenovirus knob proteins can be used as scaffolds for nano-assembly by way of incorporating a genetic mutation to produce solvent-accessible Cys residues at knob's trimeric surface. (Maye et al. *Small* 4(11), 1941-1944, 2008, incorporated herein by reference in its entirety) In contrast, the single stranded DNA with a desired sequence can be synthesized with a thiol attached to a specific base. The mixture of two systems produces a DNA-functionalized knob protein that can hybridize with other particles. The resulting symmetric tridentate linker possess tunable assembly characteristics with other nanoparticles.

The LDML strategy is based on designed linkers with multiple attachment points, which determine connections between isotropic DNA coated particles. Such linkers can possess a specific symmetry that analogously to atomic bonds will result in the particular symmetry of the formed lattice. By introducing linkers with a specific architecture of connecting sites where bonding between linker and particles is determined by molecular bonds (for example DNA, hydrogen bonds etc.) the correspondence between the linker symmetry and packing of particles into superstructures is established during the self-assembly process. This approach potentially allows for a rational fabrication of 3D structures via establishing a local connection of particles with specifically designed linkers.

(4) Fabricated "Patchy" Particles

The ability to design and assemble three-dimensional structures from colloidal particles is limited by the absence of specific directional bonds. As a result, complex or low-coordination structures, common in atomic and molecular systems, are rare in the colloidal domain. However, a general method for creating the colloidal analogues of atoms with valence: colloidal particles with chemically distinct surface patches that imitate hybridized atomic orbitals can be accomplished by cross-linking amidinated polystyrene nano/microspheres, and assembling these spheres using an emulsion-evaporation method to produce "minimal-moment" clusters with reproducible symmetries: spheres, dumbbells, triangles, tetrahedral, etc. (Monoharan V. N. et al. *Science* 301, 4830487, 2003; incorporate herein by reference in its entirety). A cluster of amidinated polystyrene spheres can then be swollen with styrene such that the extremities of the cluster protrude from the styrene droplet. The styrene is then polymerized and the protrusions from the original cluster become patches. (Ugelstad J. et al. *Makromol. Chem.* 180, 737-744, 1979; incorporate herein by reference in its entirety). In one exemplary embodiment, the patches can then be site-specifically functionalized with biotin and biotinated DNA oligomers can be introduced and bind to the particle patches via a biotin-streptavidin-biotin linkage.

Functionalized with DNA with single-stranded sticky ends, the fabricated patchy particle can form symmetric bonds through programmable, specific and reversible DNA hybridization with other nanoparticles and self-assemble into superlattices with triangular, tetrahedral and other bonding symmetries.

EXAMPLES

Example 1—Cubic Gold Nanoparticles

Cubic gold (Au) nanoparticles synthesis is described. All synthesis reagents were purchased from Sigma-Aldrich (St. Louis, Mo.) and used without further purification. Cubic nanoparticles were synthesized following the procedure outlined in Niu et al (W. X. Niu et al., *J Am Chem Soc* 131, 697 (Jan. 21, 2009); F. Lu et al., *J Am Chem Soc* 133, 18074, (Nov. 16, 2011); incorporated herein by reference in their entirety). Surfactant cetyltrimethylammonium bromide (CTAB) was used in the final seed-mediated growth of gold nanocubes. The as-synthesized nanoparticles were spun down (10 min, 8000 rpm) and re-suspended in deionized water (DIW) twice to remove excess surfactants and get concentrated suspension in DIW. Concentration of anisotropic nanoparticles was quantified using the absorbance value at the surface plasmon resonance (SPR) maximum in UV-vis absorption spectra. A molar extinction coefficient of $2.2 \times 10^{10}$ $M^{-1} \cdot cm^{-1}$ at 540 nm SPR peak was used for nanocubes with 42 nm edge.

Example 2—Octahedral Gold Nanoparticles

Similar to cubic Au nanoparticles described in Example 1, the octahedral Au nanoparticles were synthesized following the same procedure outlined in Niu et al., except instead of using CTAB surfactant, cetylpyridium chloride (CPC) surfactant was used in the final seed-mediated growth of octahedron particles. The as-synthesized nanoparticles were spun down and re-suspended in deionized water (DIW) to remove excess surfactants and get concentrated suspension in DIW. Concentration of anisotropic nanoparticles was quantified using the absorbance value at the SPR maximum in UV-vis absorption spectra. A molar extinction coefficient of $1.5 \times 10^{10}$ $M^{-1} \cdot cm^{-1}$ at 558 nm SPR peak was used for nanooctahedra with 40 nm edge.

Example 3—Spherical Gold Nanoparticles

The spherical Au nanoparticles with diameters of 38 nm and 27 nm were purchased from Ted Pella, Inc. (Redding, Calif.). The monodispersed gold nanoparticles were supplied in water, having trace amounts of citrate, tannic acid and potassium carbonate. For the Au nanospheres with diameter of 38 nm, a molar extinction coefficient of $9.3 \times 10^9$ $M^{-1} \cdot cm^{-1}$ at 529 nm was. For the Au nanospheres with diameter of 27 nm, the molar extinction coefficient of $3.6 \times 10^9$ $M^{-1} \cdot cm^{-1}$ at 527 nm was used.

The spherical Au nanoparticles with diameters of 44 nm were purchased from Nanopartz, Inc. (Loveland, Colo.). For these Au nanospheres, a molar extinction coefficient of $10 \times 10^9$ $M^{-1} \cdot cm^{-1}$ at 531 nm was used.

Example 4—DNA Functionalization of Gold Nanoparticles

Thiol-modified single-strand oligonucleotides, 5'-ATTGGATTGGAAGTA TCTTGTGTCGATAGGTCGGTTGCT-TTTTTTTTTTT-$C_6H_{12}$—SH-3' (SEQ ID NO. 1) and 5'-TACTTCCAATCCAATTCTTGTGTCGATAGGTCG-GTTGCT-TTTTTTTTTTT-$C_6H_{12}$—SH-3' (SEQ ID NO. 2) were purchased from Integrated DNA Technologies Inc. with disulfide modification. Before nanoparticle DNA functionalization, the disulfide oligonucletides were first reduced by dissolving the lyophilized samples (100300 nmoles) in 0.3 mL of a 100 mM dithiothreitol (DTT) solution in purified water or buffer. The reduced DNA was loaded onto a freshly purified sephadex column (G-25, Amersham Bioscience) and eluted with 2.5 mL of 10 mM phosphate buffer (pH=7.4). The DNA was quantified using UV-Vis analysis using the known extinction coefficient.

Au nanoparticles (AuNP) were functionalized with ssDNA following a method of J. E. Millstone et al. to achieve high DNA coverage (J. E. Millstone et al., *Small* 4, 2176 (December, 2008); incorporated herein by reference in its entirety). Briefly, an aliquot of purified DNA solution was added to 1 mL aliquot of Au nanoparticles (~3 $OD_{260}$ of DNA per mL of nanoparticle colloid). After allowing 1-3 hours for thiolated DNAs to react with the gold surface, particle suspensions were brought to 0.01% sodium dodecyl sulfate (SDS) and 10 mM sodium phosphate and allowed to sit for 1 hour. The colloidal nanoparticle solutions were then slowly treated with NaCl to allow for electrostatic screening between neighboring DNA strands and denser surface coverage of oligonucleotides. Specifically, NaCl concentration of the solution was brought to 0.5 M slowly by adding aliquots of 3 M NaCl eight times with approximately 30 minute intervals for incubation. After reaching the final NaCl concentration, particles were allowed to sit overnight to achieve maximum DNA loading. To remove the excess, unbound DNA from the solution, the mixture was centrifuged, the supernatant was removed, and the pellet was resuspended in washing buffer. This process was repeated three times. After the supernatant had been removed the third time, the pellet was resuspended in 0.2 M PBS buffer (0.2 M NaCl & 10 mM phosphate buffer, pH=7.4).

Figure 6A:
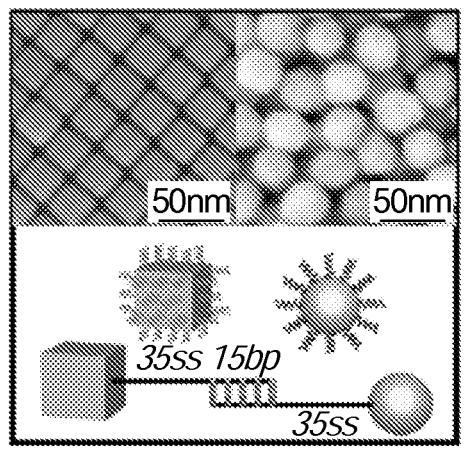
FIG. 6A shows the DNA-driven assembly of one gold spherical particle with one gold cube linker. The scanning electron microscope (SEM) image shows the contrasting organization of the cubic particles linkers (left) versus the spherical isotropic particles (right) at a resolution of 50 nm.

FIGS. 6A (left) and 7A (left) show the SEM images of individual DNA functionalized nano-cubes and octahedra, respectively, prepared as the examples of an anisotropic particle linker. FIGS. 6A (right) and 7A (right) show the SEM images of individual spherical nanoparticles. Since the DNA sequences are not self-complementary, the cubes, octahedra and spheroids do not self-assemble in a solution into a superlattice.

Example 5—Superlattice Formation from Cubic and Spherical Nanoparticles

After the Au nanoparticles (linkers and spheres) functionalization with ssDNA in Example 4, the assembly was obtained by combing equal molar amounts of DNA-capped (SEQ ID NO. 1) gold nanocubes and DNA-capped (SEQ ID NO. 2) gold nanospheres. The samples were then aggregate at room temperature, annealed at 58° C. for about 30 minutes and cooled down to room temperature for about 2 hours. The resulting precipitate was collected and transferred in buffer to a quartz capillary (1.0 mm diameter), and sealed with wax.

Figure 6B:
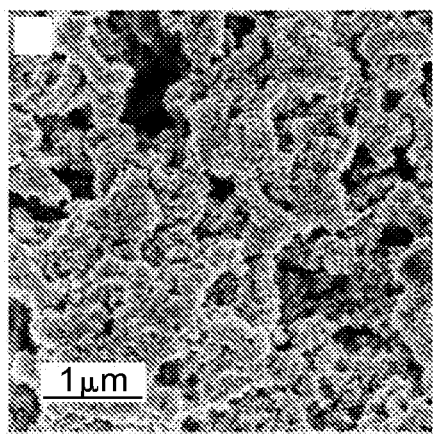
FIG. 6B-6C show the SEM image of the DNA-driven assembly of the structures of FIG. 6A (gold spherical particles together with gold cube linkers) at a resolution of 1 µm (B) and 50 nm (C).
Figure 6C:
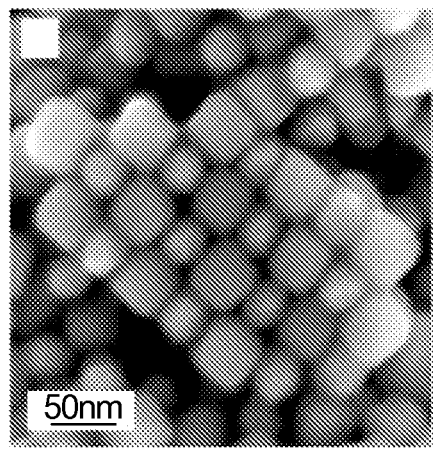
Figure 6D:
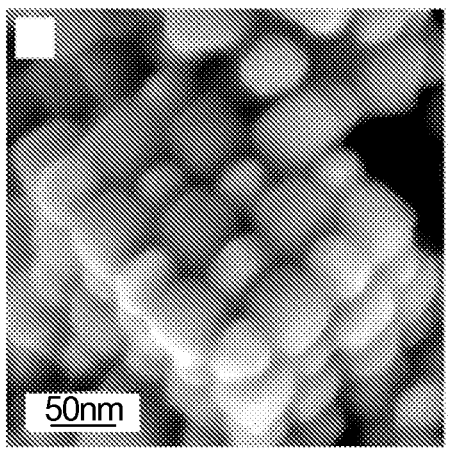
FIG. 6D shows the structures of FIG. 6C tilted.

The samples deposited on a cleaned silicon substrate were measured using Hitachi S-4800 Scanning Electron Microscopy with typical 1 kV voltage and 10 μA emission current. A standard polyelectrolyte-assisted layer-by-layer (LBL) method was applied to preparing the diluted nanoparticles-assembled clusters for SEM characterization (S. Vial, et al. *Langmuir* 23, 4606 (Apr. 10, 2007) incorporated herein by reference in its entirety). Silicon wafers were used as substrates for SEM characterization. The substrates were sonicated for 10 min in water and then in ethanol, subsequently thoroughly cleaned using piranha solution ($H_2SO_4:H_2O_2=7:3$), rinsed with deionized water, and dried under an air stream. The wafers were stored in water until use. Before used, the wafers were first immersed in an aqueous solution of positively charged poly (diallydimethylammounium chloride) PDDA (Mw=200000, 1 mg/mL in 0.5 M NaCl aqueous solution) for 20 min, then in an aqueous solution of the polyanion poly(acrylic acid, sodium salt) PAA (Mw=15000, 1 mg/mL in 0.5 M NaCl aqueous solution) for 10 min, and finally in PDDA solution for 10 min. At this stage, the wafers are positively charged, favoring the electrostatic interaction with negatively charged DNA in the assembled aggregates. To obtain a monolayer of nanoparticles-assembled clusters, the pretreated wafers were immerse into the corresponding solution with diluted aggregates and kept for a suitable period time. After enough absorption, the substrates were rinsed with deionized water and dried under an air stream for further SEM characterization. FIGS. 6B and 6C show the scanning electron microscope (SEM) images of the DNA-driven assembly of Au DNA-capped nanospheres and nanocubes at a resolution of 1 μm and 50 nm, respectively. FIG. 6D shows the generated Au superlattice slightly tilted from the conformation seen in FIG. 6C.

Figure 6F:
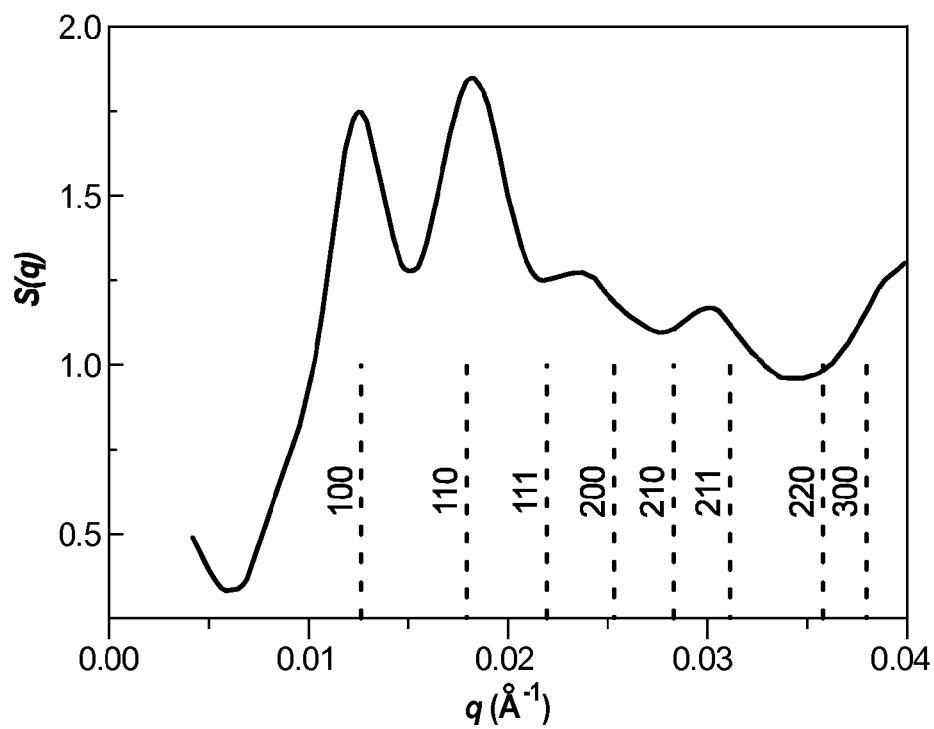
FIG. 6F is an idealized visualization of the formed simple cubic lattice of NaCl-type, where spheres are organized by cube linkers.
Figure 6F:
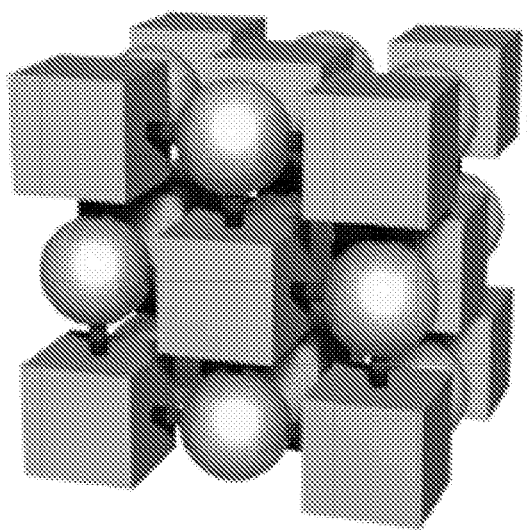

SAXS experiments were performed in-situ at the National Synchrotron Light Source's (NSLS) X9 beamline. The scattering data were collected with a MarCCD area detector and converted to 1D scattering intensity vs. wave vector transfer, $q=(4\pi/\lambda) \sin(\theta/2)$, where $\lambda=0.9184$ Å, and $\theta$, are the wavelength of incident X-ray and the scattering angle respectively. The data are presented as the structure factor S (q), which was calculated as Ia (q)/Ip(q), where Ia (q) and Ip(q) are background corrected 1D scattering intensities extracted by angular averaging of CCD images for a system under consideration and the corresponding unaggregated gold particles, respectively. The peak positions in S (q) are determined by fitting a Lorenzian form. The plot obtained by small angle x-ray scattering (SAXS) of the assembly shown in FIG. 6E reveals that the assembly SAXS lines and indexing align with simple cubic model (see FIG. 6F).

Example 6—Quantify the Ordering of Cube-Sphere Assemblies

Figure 9A:
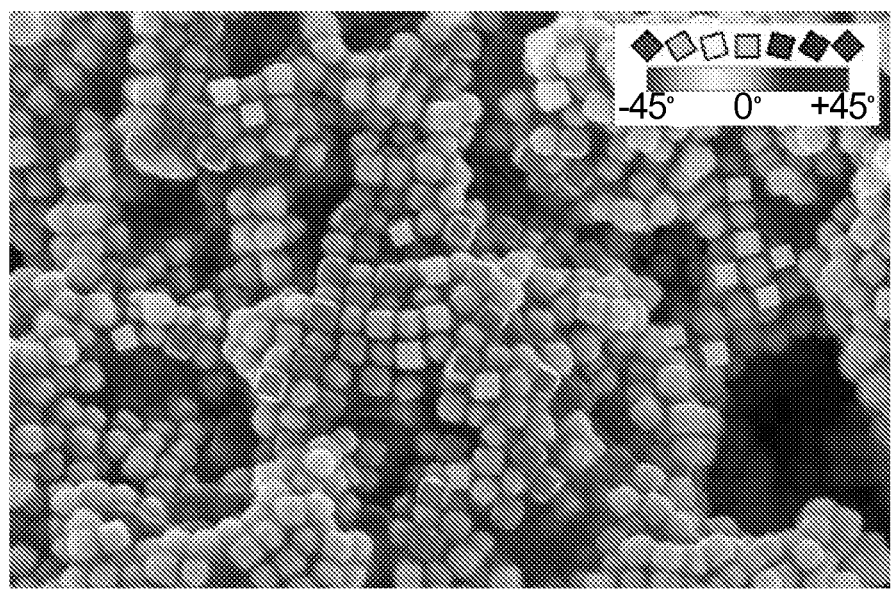
FIG. 9A is an SEM image of 42 nm cube-sphere assemblies for 44 nm spheres, the lower image for 27 nm spheres. A selection of cubes have been coded according to their orientation (inset legend describes code).
Figure 9B:
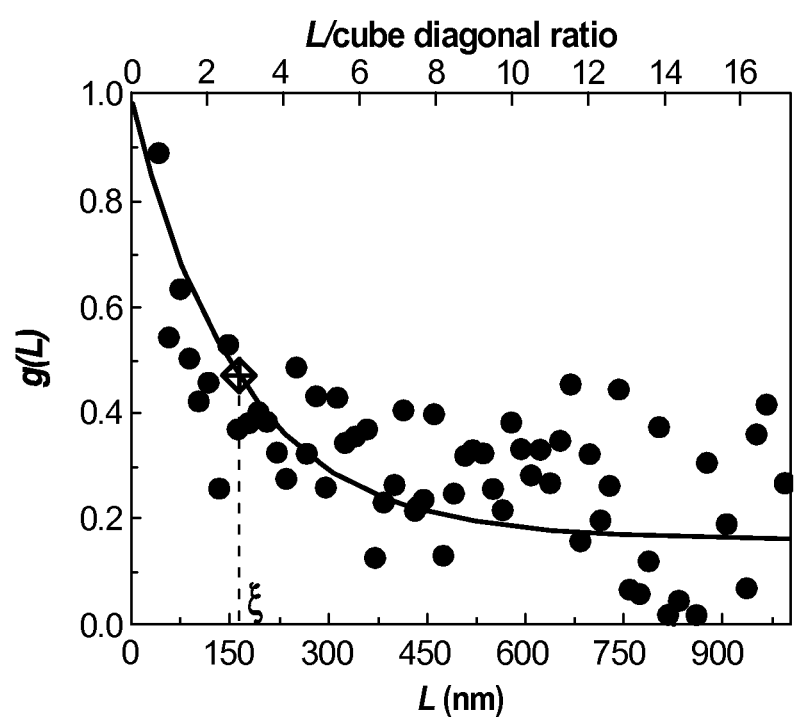
FIG. 9B is a plot showing order correlation analysis of the cube-sphere binary assembly in FIG. 9A (ξ is 164 nm).

In order to quantify the ordering of the cube-sphere assemblies, the orientation of a selection of cubes within scanning electron micrographs (SEM) were manually determined. The cubes appear effectively as square, and the orientation of these 4-fold symmetric objects can be described using an angle $-45°<\alpha<+45°$. Examples images are shown in FIG. 9. It must be noted that for the 38 nm sphere assemblies, nearby cubes have similar orientations: there is a strong orientation correlation that extends over many lattice repeats. By comparison, the 27 nm spheres create assemblies that are poorly ordered: nearby cubes have little correlation between their orientations. To quantify this correlation effect, an orientation correlation function, g(r), was calculated as a function of separation distance r. First, an order parameter for a cube at position r can be determined using: $\psi(r)=e^{4i\alpha(r)}$. The orientational correlation function is then computed as:

$$g(r)=<\psi(0)\psi(r)>,$$

where the angle brackets average over all the pairwise particle correlations. The function g(r) decays from a value of exactly 1.0 (each particle is correlated perfectly with itself) to 0.0 in the limit of there being no correlation. By fitting the decay of g(r) to an exponential function, a characteristic lengthscale, the orientational correlation length $\xi$ is obtained, which can be used as an estimate of the average grain size for the superlattice. It must be noted that $\xi_{37\ nm}=217$ nm and $\xi_{27\ nm}=44$ nm, indicating that the larger spheres generate well-ordered assemblies with enforced order over 4-6 lattice repeats; whereas the small spheres do so substantially less.

Figure 10:
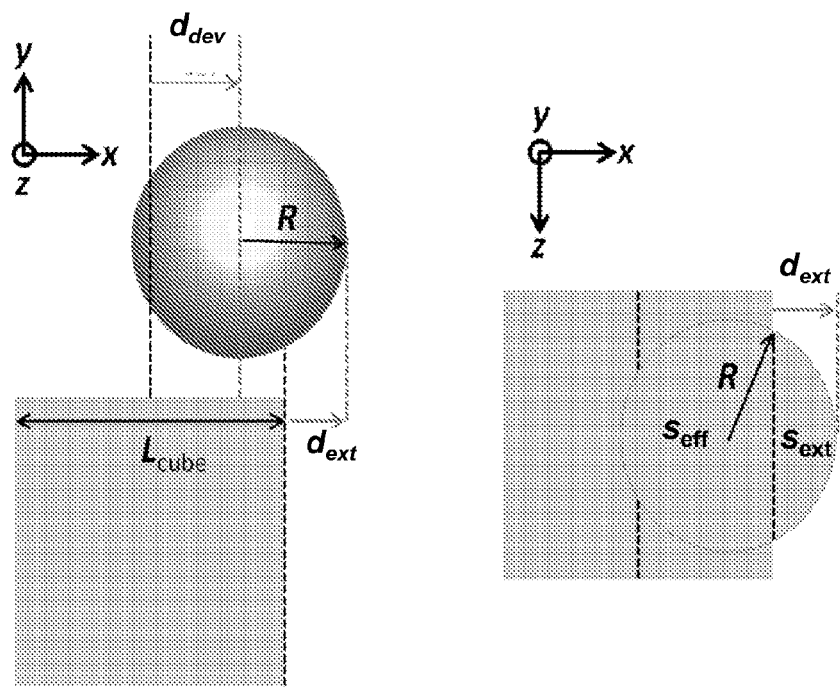
FIG. 10 is a scheme of a cube-sphere pair as a model for calculation of attraction potential energy. The left image is a side-view and the right one is a top-view.

Example 7—Modeling and Calculation of Attraction Potential Energy Between Cube and Sphere Total hybridization energy of DNA bridges between a sphere (radius of R) and a cube (edge length of $L_{cube}$) dominates the pair attraction potential energy, $\Delta E_{att}$, which is proportional to the number of hybridized DNA bridges formed between the their contradictory surfaces, with van der Waals (vdW) interactions contributing insignificantly. When $2R \leq L_{cube}$, the number of hybridized DNA bridges formed between sphere and cube is approximately proportional to the circle projection area of sphere on the square facet of cube, i.e., effective area, $S_{eff}$, which can be obtained from simple geometry considerations as (see FIG. 10):

$$S_{eff} = S_{ful} - S_{ext}$$

$$S_{ful} = \pi R^2$$

$$S_{ext} = R^2\left[\cos^{-1}\left(\frac{R-d_{ext}}{R}\right)\right] - (R-d_{ext})\sqrt{R^2-(R-d_{ext})^2}$$

$$S_{eff} = \pi R^2 + (R-d_{ext})\sqrt{d_{ext}(2R-d_{ext})} - R^2\left[\cos^{-1}\left(\frac{R-d_{ext}}{R}\right)\right]$$

Where $S_{ful}$ is the surface area of the full sphere projection with radius of R; $S_{ext}$ is the surface area of the extruding projection that is excluded from square facet of cube with a distance of $d_{ext}$.

When sphere deviates from the origin with a distance of $d_{dev}$, the pair attraction potential energy can be approximated as follows:

$$\Delta E_{att}(R, d_{dev}) \propto S_{eff} = \begin{cases} \pi R^2 & \left(0 \le d_{dev} \le \frac{L_{cube}}{2} - R\right) \\ \pi R^2 + (R - d_{ext})\sqrt{d_{ext}(2R - d_{ext})} - R^2\left[\cos^{-1}\left(\frac{R - d_{ext}}{R}\right)\right], \\ d_{ext} = d_{dev} - \frac{L_{cube}}{2} + R, & \left(\frac{L_{cube}}{2} - R < d_{dev} \le \frac{L_{cube}}{2}\right) \end{cases}$$

Considering compare convenience, the pair attraction potential energy can be normalized by $|\Delta E_{att}(R,0)|$.

Example 8—Superlattice Formation from Octahedral and Spherical Nanoparticles

Figure 7A:
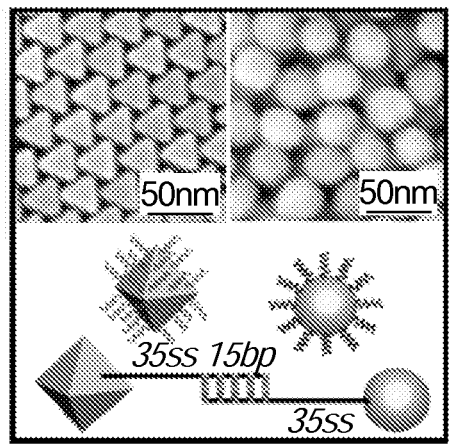
FIG. 7A shows the DNA-driven assembly of one gold spherical particle with one gold octahedral linker. The scanning electron microscope (SEM) image shows the contrasting organization of the octahedra (linkers) versus the spherical isotropic particles.
Figure 7B:
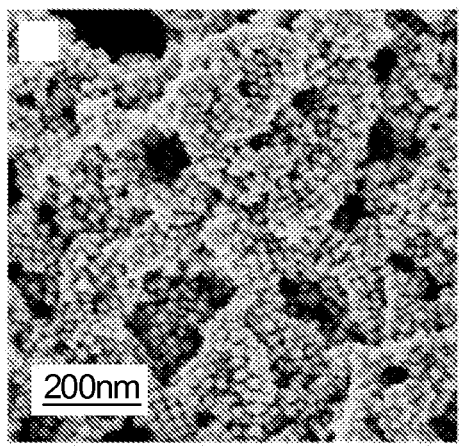
FIG. 7B-7D show the SEM image of the DNA-driven assembly of the structures of FIG. 7A (gold spherical particles together with gold octahedral linkers) at a resolution of 200 nm (B), 50 nm (C), and 20 nm tilted (D).
Figure 7C:
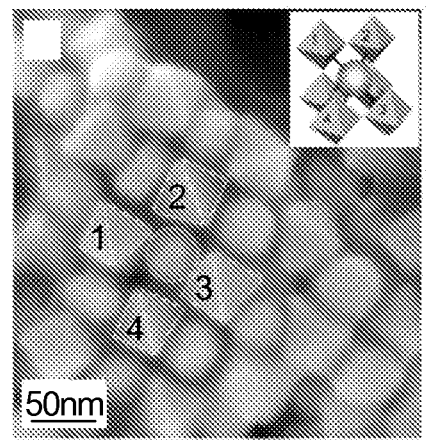
Figure 7D:
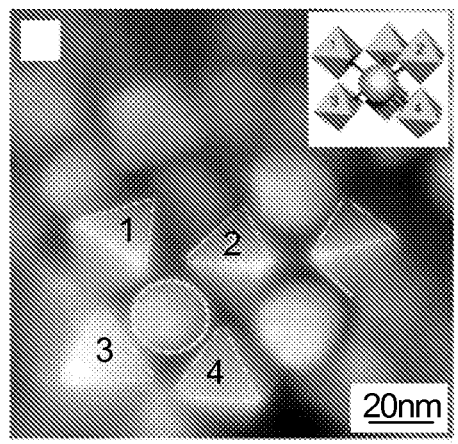
Figure 7E:
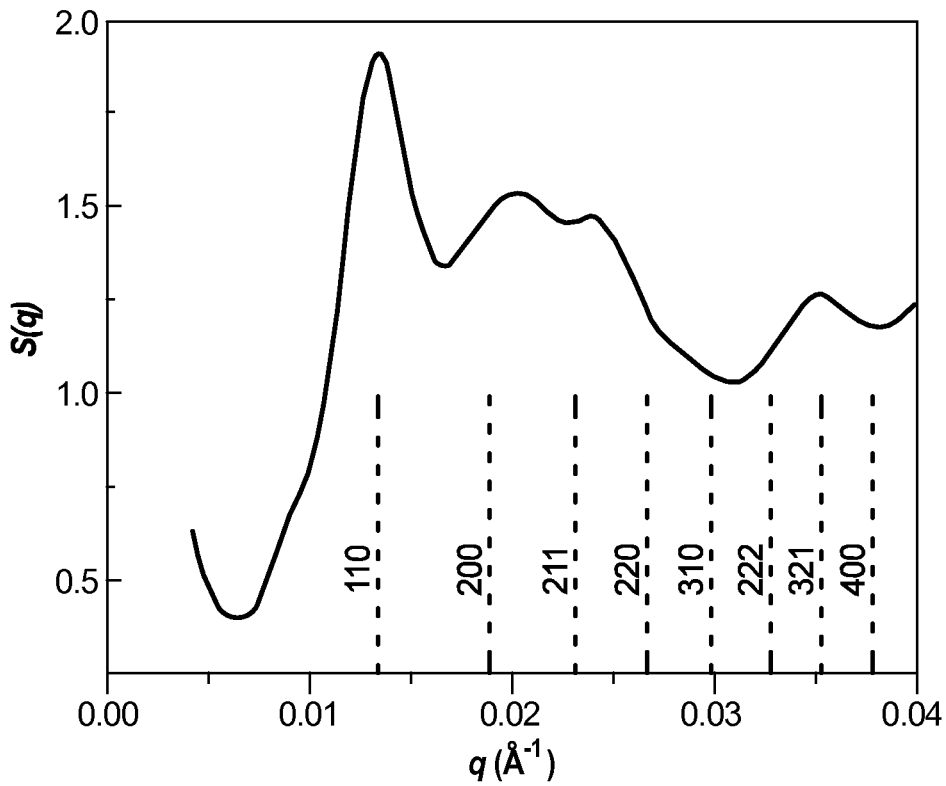
FIG. 7E is a plot obtained by SAXS of the assembly in FIGS. 7B-7D. The plot reveals the assembly lines and indexing with cubic perovskite model.
Figure 7F:
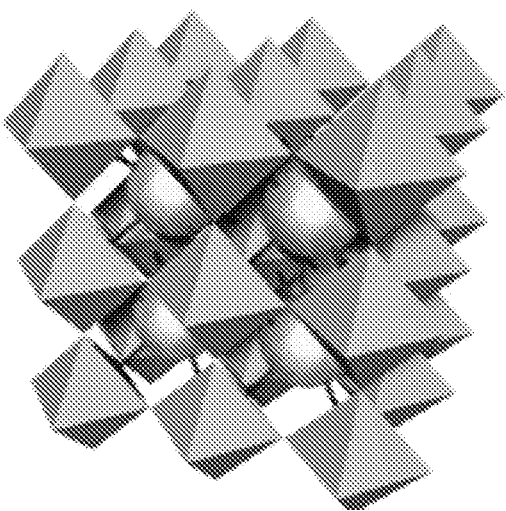
FIG. 7F is an idealized visualization of the formed lattice (perovskite-type) of spheres organized by octahedra linkers.

After the Au nanoparticles (linkers and spheres) functionalization with ssDNA, the assembly was obtained by combing equal molar amounts of SEQ ID NO. 1 and SEQ ID NO. 2 DNA-capped gold nanoparticles and the particles were allowed to aggregate at room temperature. The samples were then annealed at 58° C. for about 30 mins and cooled down to room temperature for about 2 hours. The resulting precipitate was collected and transferred in buffer to a quartz capillary (1.0 mm diameter), and sealed with wax. FIGS. 7B and 7C show the scanning electron microscope (SEM) images of the DNA-driven assembly of Au DNA-capped nanospheres and nanooctahedra at a resolution of 200 nm and 50 nm, respectively. FIG. 7D shows the generated Au superlattice slightly tilted from the conformation seen in FIG. 7C and at a resolution of 20 nm. The plot obtained by small angle x-ray scattering (SAXS) of the assembly shown in FIG. 7E reveals that the assembly SAXS lines and indexing align with cubic perovskite model (see FIG. 7F).

Example 9—Preparation of the DNA Tetrahedron

The DNA tetrahedra with high melting temperature were prepared from four DNA single strands based on the procedure described in He, Y. et al. (*Nature* 452, 198-201, 2008; incorporated herein by reference in its entirety).

Figure 11:
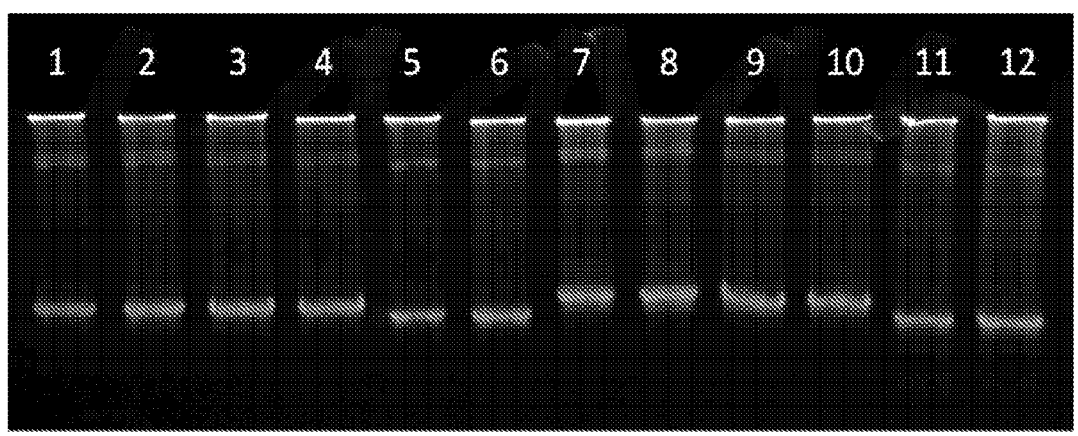
FIG. 11 shows an image of 6% polyacrylamide non-denaturing gel electrophoresis for twelve samples: the self-assembled DNA tetrahedra with different number of arms, under different buffer conditions and with or without heat treatment after assembly.

To check the stoichiometry of four DNA single strands, the structural uniformity and the thermal stability of the DNA tetrahedral scaffolds, the self-assembled DNA tetrahedra were examined by gel electrophoresis. FIG. 11 shows a 6% polyacrylamide non-denaturing gel electrophoresis for twelve samples described in Table 1. Sets of strands for constructing the DNA tetrahedra were stoichiometrically mixed and dissolved to 1.0 µM in 1×TAE buffer (40 mM Tris-acetate, 1 mM EDTA, pH 8.3) with respective amounts of magnesium acetate and sodium chloride that meet the conditions in Table 1.

After assembling the scaffolds, the samples for Lane 4 and 10 were heated up to 50° C. for 3 min and cooled down quickly to check the thermal stability for crystallization process. Then equimolar amounts (2.5 pmol) of DNA tetrahedra, with respective conditions, were loaded into all wells. The gel was run at 200 V for 1 hour and stained with ethidium bromide for 3 min. Some of DNA tetrahedral scaffolds appear to aggregate each other with their arms and are accumulating in each well. However, a single high-intensity band corresponds to the single DNA tetrahedra has appeared in each lane, indicating the high-yield and the uniform assembly of DNA tetrahedral scaffolds. Regardless of how many bases the connecting bond has, melting temperature of DNA tetrahedron is determined by the thermal stability of double-stranded tetrahedra scaffold. By gel electrophoresis assay after heating up to 50 degree C. (in Lane 4 and 10), there was no significant structural change in DNA tetrahedra.

The DNA scaffolds require a certain amount of magnesium and/or sodium ions to structurally stabilize the duplex. However, these ions sometimes accelerate the aggregation of DNA-covered AuNPs. Therefore, the influence of magnesium and sodium ion concentrations was checked for DNA-covered Au nanoparticles by DLS before crystallization with DNA tetrahedra. The DNA-covered AuNPs had a diameter of ~20 nm (corresponds to AuNP with DNA shell) and they did not aggregate under the concentration of $Mg^{2+}$ below 5 mM. Some AuNP aggregation was observed under the concentration of $Mg^{2+}$ over 6 mM. However, no aggregation occurred during assembling of DNA tetrahedra and AuNPs under the concentration of $Mg^{2+}$ over 6 mM and almost the same sharpness of peaks was confirmed for each sample in different buffers

Example 10—Diamond Lattice Formation

DNA-covered AuNPs and DNA tetrahedra were mixed in capillary tubes under (1) different conditions; (2) ratio of DNA tetrahedra to AuNPs, (3) length of flexor and recognition sequence region and (4) ion concentration (see Table 1). After assembling, the clear supernatants have been confirmed in the capillary tubes with equimolar mixtures of DNA tetrahedra and AuNPs, indicating an assembly with equimolar ratio. The remaining red-colored supernatants in tetrahedral-AuNP mixtures indicates suspending AuNPs covered with excessive DNA tetrahedra. Some of the same samples were assembled in different buffer conditions, different $Na^+$ and $Mg^{2+}$ concentrations, however, there was no significant difference between the structures of assembled crystals in different buffers.

To test how the size of the DNA influences the formation of the lattice, six tetrahedra systems were prepared (System I-VI) with varying DNA sequence length of the recognition site as summarized in Table 2.

TABLE 1

| Lane | 1 | 2 | 3 | 4 | 5 | 6 | 7 | 8 | 9 | 10 | 11 | 12 |
|---|---|---|---|---|---|---|---|---|---|---|---|---|
| Number of arms | 4 | 4 | 4 | 4 | 3 | 3 | 4 | 4 | 4 | 4 | 3 | 3 |
| $Na^+$ concentration (mM) | 1 | – | – | – | 1 | – | 1 | – | – | – | 1 | – |
| $Mg^{2+}$ concentration (mM) | – | 12 | 6 | 6 | – | 12 | – | 12 | 6 | 6 | – | 12 |
| Heat treatment at 50° C. | – | – | – | + | – | – | – | – | – | + | – | – |

TABLE 2

DNA sequences used to construct a tetrahedron

System I
TACTTCCAATCCAAT-tttttttttt-ccc tgt act ggc tag gaa ttc acg ttt     AtetE37t10-1-dn15
taa tct ggg ctt ggg tta aga aac tcc ccg cgc tgg agg cgc atc acc gtt gcg     (SEQ ID NO. 3)
tat gtg ttc tgt gcg gcc tgc cgt ccc gtg tgg g
TACTTCCAATCCAAT-tttttttttt-cgg tga tgc gcc tcc agc gcg ggg     AtetE37t10-2-dn15
agt ttc tta acc ctt ccg act tac aag agc cgg gcg aga ctc agg tgg tgc ctt     (SEQ ID NO. 4)
ggc att cga cca gga gat atc gcg ttc agc tat gcc c
TACTTCCAATCCAAT-tttttttttt-ccc atg aga ata ata ccg ccg att tac     AtetE37t10-3-dn15
gtc agt ccg gtt ccc aca cgg gac ggc agg ccg cac aga aca cat acg ctt     (SEQ ID NO. 5)
ggg cat agc tga acg cga tat ctc ctg gtc gaa tgc c
TACTTCCAATCCAAT-tttttttttt-gcc cag att aaa acg tga att cct     AtetE37t10-4-dn15
agc cag tac agg gtt ccg gac tga cgt aaa tcg gcg gta tta ttc tca tgg gtt     (SEQ ID NO. 6)
ggc acc acc tga gtc tcg ccc ggc tct tgt aag tcg g System II
TACTTCCAATCCAAT-ttttt-ccc tgt act ggc tag gaa ttc acg ttt taa     AtetE37t5-1-dn15
tct ggg ctt ggg tta aga aac tcc ccg cgc tgg agg cgc atc acc gtt gcg tat     (SEQ ID NO. 7)
gtg ttc tgt gcg gcc tgc cgt ccc gtg tgg g
TACTTCCAATCCAATttttt cgg tga tgc gcc tcc agc gcg ggg agt     AtetE37t5-2-dn15
ttc tta acc ctt ccg act tac aag agc cgg gcg aga ctc agg tgg tgc ctt ggc     (SEQ ID NO. 8)
att cga cca gga gat atc gcg ttc agc tat gcc c
TACTTCCAATCCAATttttt ccc atg aga ata ata ccg ccg att tac gtc     AtetE37t5-3-dn15
agt ccg gtt ccc aca cgg gac ggc agg ccg cac aga aca cat acg ctt ggg     (SEQ ID NO. 9)
cat agc tga acg cga tat ctc ctg gtc gaa tgc c
TACTTCCAATCCAATttttt gcc cag att aaa acg tga att cct agc cag     AtetE37t5-4-dn15
tac agg gtt ccg gac tga cgt aaa tcg gcg gta tta ttc tca tgg gtt ggc acc     (SEQ ID NO. 10)
acc tga gtc tcg ccc ggc tct tgt aag tcg g System III
TTCCAATCCAATttttt ccc tgt act ggc tag gaa ttc acg ttt taa tct     TetT5R12-1
ggg ctt ggg tta aga aac tcc ccg cgc tgg agg cgc atc acc gtt gcg tat     (SEQ ID NO. 11)
gtg ttc tgt gcg gcc tgc cgt ccc gtg tgg g
TTCCAATCCAATttttt cgg tga tgc gcc tcc agc gcg ggg agt ttc tta     TetT5R12-2
acc ctt ccg act tac aag agc cgg gcg aga ctc agg tgg tgc ctt ggc att     (SEQ ID NO. 12)
cga cca gga gat atc gcg ttc agc tat gcc c
TTCCAATCCAATttttt ccc atg aga ata ata ccg ccg att tac gtc agt     TetT5R12-3
ccg gtt ccc aca cgg gac ggc agg ccg cac aga aca cat acg ctt ggg cat     (SEQ ID NO. 13)
agc tga acg cga tat ctc ctg gtc gaa tgc c
TTCCAATCCAATttttt gcc cag att aaa acg tga att cct agc cag tac     TetT5R12-4
agg gtt ccg gac tga cgt aaa tcg gcg gta tta ttc tca tgg gtt ggc acc acc     (SEQ ID NO. 14)
tga gtc tcg ccc ggc tct tgt aag tcg g System IV
CCAATCCAATtt ccc tgt act ggc tag gaa ttc acg ttt taa tct ggg ctt     TetT2R10-1
ggg tta aga aac tcc ccg cgc tgg agg cgc atc acc gtt gcg tat gtg ttc tgt     (SEQ ID NO. 15)
gcg gcc tgc cgt ccc gtg tgg g
CCAATCCAATtt cgg tga tgc gcc tcc agc gcg ggg agt ttc tta acc ctt     TetT2R10-2
ccg act tac aag agc cgg gcg aga ctc agg tgg tgc ctt ggc att cga cca     (SEQ ID NO. 16)
gga gat atc gcg ttc agc tat gcc c
CCAATCCAATtt ccc atg aga ata ata ccg ccg att tac gtc agt ccg gtt     TetT2R10-3
ccc aca cgg gac ggc agg ccg cac aga aca cat acg ctt ggg cat agc tga     (SEQ ID NO. 17)
acg cga tat ctc ctg gtc gaa tgc c
CCAATCCAATtt gcc cag att aaa acg tga att cct agc cag tac agg gtt     TetT2R10-4
ccg gac tga cgt aaa tcg gcg gta tta ttc tca tgg gtt ggc acc acc tga gtc     (SEQ ID NO. 18)
tcg ccc ggc tct tgt aag tcg g System V
AATCCAATtt ccc tgt act ggc tag gaa ttc acg ttt taa tct ggg ctt ggg     TetT2R8-1
tta aga aac tcc ccg cgc tgg agg cgc atc acc gtt gcg tat gtg ttc tgt gcg     (SEQ ID NO. 19)
gcc tgc cgt ccc gtg tgg g
AATCCAATtt cgg tga tgc gcc tcc agc gcg ggg agt ttc tta acc ctt     TetT2R8-2
ccg act tac aag agc cgg gcg aga ctc agg tgg tgc ctt ggc att cga cca     (SEQ ID NO. 20)
gga gat atc gcg ttc agc tat gcc c
AATCCAATtt ccc atg aga ata ata ccg ccg att tac gtc agt ccg gtt ccc     TetT2R8-3
aca cgg gac ggc agg ccg cac aga aca cat acg ctt ggg cat agc tga acg     (SEQ ID NO. 21)
cga tat ctc ctg gtc gaa tgc c
AATCCAATtt gcc cag att aaa acg tga att cct agc cag tac agg gtt     TetT2R8-4
ccg gac tga cgt aaa tcg gcg gta tta ttc tca tgg gtt ggc acc acc tga gtc     (SEQ ID NO. 22)
tcg ccc ggc tct tgt aag tcg g System VI
CCAATCCAATt ccc tgt act ggc tag gaa ttc acg ttt taa tct ggg ctt     TetT1R10-1_1031
ggg tta aga aac tcc ccg cgc tgg agg cgc atc acc gtt gcg tat gtg ttc tgt     (SEQ ID NO. 23)
gcg gcc tgc cgt ccc gtg tgg g
CCAATCCAATt cgg tga tgc gcc tcc agc gcg ggg agt ttc tta acc ctt     TetT1R10-2_1031
ccg act tac aag agc cgg gcg aga ctc agg tgg tgc ctt ggc att cga cca     (SEQ ID NO. 24)
gga gat atc gcg ttc agc tat gcc c
CCAATCCAATt ccc atg aga ata ata ccg ccg att tac gtc agt ccg gtt     TetT1R10-3_1031
ccc aca cgg gac ggc agg ccg cac aga aca cat acg ctt ggg cat agc tga     (SEQ ID NO. 25)
acg cga tat ctc ctg gtc gaa tgc c
CCAATCCAATt gcc cag att aaa acg tga att cct agc cag tac agg gtt     TetT1R10-4_1031
ccg gac tga cgt aaa tcg gcg gta tta ttc tca tgg gtt ggc acc acc tga gtc     (SEQ ID NO. 26)
tcg ccc ggc tct tgt aag tcg g To assemble a DNA tetrahedron, four equimolar amounts of DNA (T1-T4) were combined together to initiate cross-hybridization (SEQ ID NOs. 3-6; 7-10, 11-14, 15-18, 19-22, 23-26). The four single stranded (ss) DNA molecules (see FIG. 8A; System VI shown) were encoded to only hybridize with each other in a specific location and manner.

```
ATTGGATTGGAAGTAttttt----- tttttttTAACCTAACC (System VI)
```

Figure 8B:
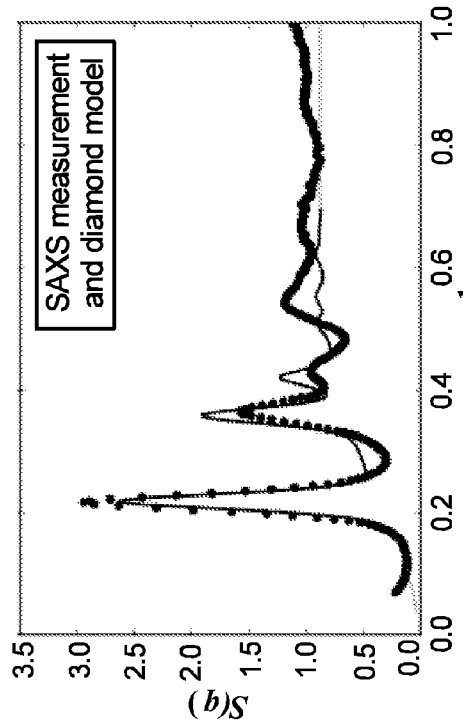
FIG. 8B is a plot of the measured structure factor S(q) from SAXS (dots) in comparison to a modeled diamond lattice (solid line).
Figure 8D:
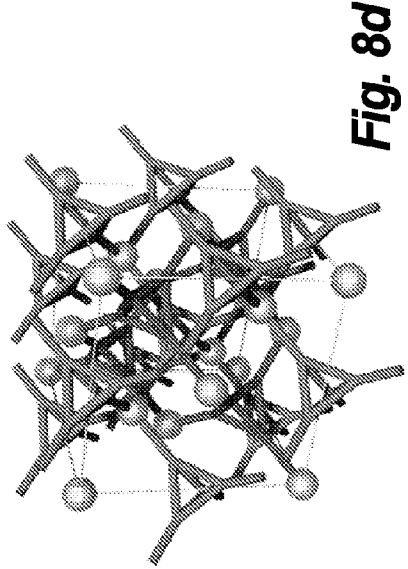
FIG. 8D is a model of the tetrahedron-driven assembly of spherical particles that form a diamond type structure from spheres and tetrahedron DNA linkers.
Figure 8A:
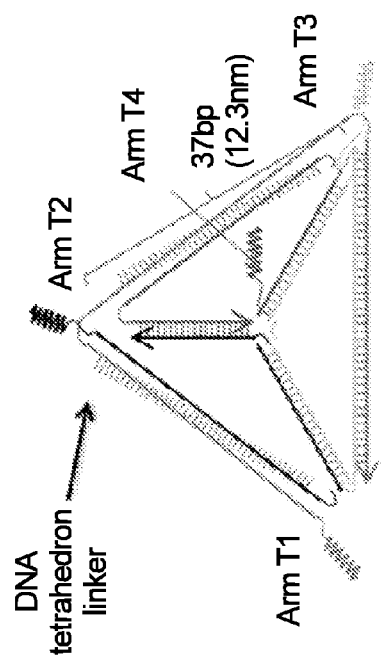
FIG. 8A is an illustration of the DNA tetrahedron linker formed by four DNA strands (T1-T4). The insert shows a 3D model of the DNA tetrahedron.

As illustrated in FIG. 8A, DNA T1 has four regions of 37 base pairs (~12.3 nm) (System VI). The first T1 region hybridized with the first region of T2 to form a double stranded helix. The second T1 region hybridized with the second T4 region. The third T1 region hybridized with the third T3 region. Each 5' end of single strand (T1-T4) coming out from vertex has a recognition site as connecting bond. Each connecting bond consists of poly-T flexible part (flexor) and recognition sequence.

Figure 8C:
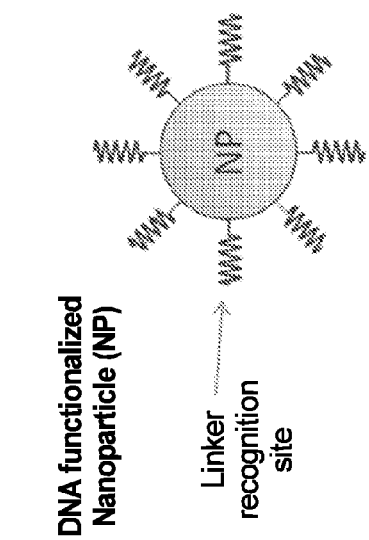
FIG. 8C shows a DNA functionalized nanoparticle that is attached at each DNA strand (T1-T4).

The recognition sequence was used to hybridize with the DNA functionalized Au nanoparticles prepared in Example 3 to form DNA-nanoparticle construct (see FIG. 8C). Specifically, the recognition sequence of four symmetrical connecting bonds was complementary to the ones of single strands from AuNPs. The AuNPs, mediated by DNA tetrahedra, assembled into large-scale ordered structures through annealing process. By changing the lengths of flexor and recognition sequence, flexibility of connections between particles and melting temperature of crystal was examined. It was observed that all sequences (I to VI) result in tetrahedra formation and are suitable for lattice formation.

Although more rigid ones show a better structural organization (I>II>III>IV>V>VI). That is, it was found that 1-2 nucleotides in a flexor resulted in the best structures. While these examples illustrate a tetrahedron with identical recognition sites, it is also within scope of this disclosure to use different recognition site sequences, thereby specifically linking different particles to the same linker DNA construct.

The measurements from the small-angle x-ray scattering (SAXS) experiments (see FIG. 8B) suggest that nanoparticles with the DNA scaffold tetrahedron form superlattices having a diamond shape symmetry (see FIG. 8D). While assembly of spherical particle typically results in a body-centered cubic (BCC) lattice, the DNA tetrahedron linker forces the formation of diamond type lattice of spherical particles. Similarly, the same particles can be assembled into any of the 230 known lattices by selecting an appropriate linker particle with specific symmetry of connecting sites.

It will be appreciated by persons skilled in the art that the present invention is not limited to what has been particularly shown and described. Rather, the scope of the present invention is defined by the claims which follow. It should further be understood that the above description is only representative of illustrative examples of embodiments. The description has not attempted to exhaustively enumerate all possible variations. The alternate embodiments may not have been presented for a specific portion of the invention, and may result from a different combination of described portions, or that other undescribed alternate embodiments may be available for a portion, is not to be considered a disclaimer of those alternate embodiments. It will be appreciated that many of those undescribed embodiments are within the literal scope of the following claims, and others are equivalent.

The invention claimed is:

1. A controllable nanoparticle superlattice comprising,
a linker comprising a specified symmetry of connecting sites, wherein the linker is a symmetric DNA scaffold construct, an anisotropic particle, a multimeric protein-DNA complex, or a "patchy" particle, and wherein the connecting sites of the linker have non-complementary DNA and/or RNA attached thereto; and
a nanoparticle encapsulated with non-complementary DNA and/or RNA, wherein the non-complementary DNA and/or RNA of the nano particle is complementary to the non-complementary DNA and/or RNA of the linker so as to form a nanoparticle superlattice, wherein the symmetry of the superlattice is determined by the specified symmetry of the connecting sites of the linker.

2. The controllable nanoparticle superlattice according to claim 1, wherein the linker is a symmetric DNA scaffold construct or an anisotropic particle.

3. The controllable nanoparticle superlattice according to claim 1, wherein the the linker is a symmetric DNA scaffold construct.

4. The controllable nanoparticle superlattice according to claim 3, wherein the symmetric DNA scaffold construct has one of a cubic geometry, tetrahedron geometry, or octahedron geometry.

5. The controllable nanoparticle superlattice according to claim 4, wherein the symmetric DNA scaffold construct is a DNA tetrahedron.

6. The controllable nanoparticle superlattice according to claim 1, wherein the formed nanoparticle superlattice is a diamond lattice, simple cubic lattice or perovskite lattice.

7. The controllable nanoparticle superlattice according to claim 1, wherein the anisotropic particle has connecting sites at particle facets.

8. The controllable nanoparticle superlattice according to claim 1, wherein the anisotropic particle has connecting sites at particle vertices.

9. The controllable nanoparticle superlattice according to claim 1, wherein the anisotropic particle is metal.

10. The controllable nanoparticle superlattice according to claim 9, wherein the metal is selected from the group consisting of gold, silver, and platinum.

11. The controllable nanoparticle superlattice according to claim 1, wherein the linker is an anisotropic particle comprising a semiconductor.

12. The controllable nanoparticle superlattice according to claim 11, wherein the semiconductor is selected from the group consisting of cadmium selenide, cadmium sulfide, zinc sulfide, and gallium arsenide.

13. The controllable nanoparticle superlattice according to claim 1, wherein the linker is a magnetic anisotropic particle.

14. The controllable nanoparticle superlattice according to claim 13, wherein the magnetic anisotropic particle is iron oxide.

15. The controllable nanoparticle superlattice according to claim 1, wherein the linker is an anisotropic particle comprising silicon dioxide.

16. The controllable nanoparticle superlattice according to claim 1, wherein the linker is a multimeric protein-DNA complex comprising a knob adenovirus protein or streptavidin tetramer.

* * * * *

SEQUENCE LISTING

<160> NUMBER OF SEQ ID NOS: 28

<210> SEQ ID NO 1
<211> LENGTH: 50
<212> TYPE: DNA
<213> ORGANISM: Artificial Sequence
<220> FEATURE:
<223> OTHER INFORMATION: Complementary sequence for particle
      functionalization

<400> SEQUENCE: 1
attggattgg aagtatcttg tgtcgatagg tcggttgctt ttttttttt            50

<210> SEQ ID NO 2
<211> LENGTH: 50
<212> TYPE: DNA
<213> ORGANISM: Artificial Sequence
<220> FEATURE:
<223> OTHER INFORMATION: Complementary sequences for particle
      functionalization

<400> SEQUENCE: 2
tacttccaat ccaattcttg tgtcgatagg tcggttgctt ttttttttt            50

<210> SEQ ID NO 3
<211> LENGTH: 140
<212> TYPE: DNA
<213> ORGANISM: Artificial Sequence
<220> FEATURE:
<223> OTHER INFORMATION: Tetrahedron DNA construct

<400> SEQUENCE: 3

```
tacttccaat ccaattttt tttttccctg tactggctag gaattcacgt tttaatctgg      60
gcttgggtta agaaactccc cgcgctggag gcgcatcacc gttgcgtatg tgttctgtgc    120
ggcctgccgt cccgtgtggg                                                140

<210> SEQ ID NO 4
<211> LENGTH: 140
<212> TYPE: DNA
<213> ORGANISM: Artificial Sequence
<220> FEATURE:
<223> OTHER INFORMATION: Tetrahedron DNA construct

<400> SEQUENCE: 4
tacttccaat ccaattttt tttttcggtg atgcgcctcc agcgcgggga gtttcttaac      60
ccttccgact tacaagagcc gggcgagact caggtggtgc cttggcattc gaccaggaga    120
tatcgcgttc agctatgccc                                                140

<210> SEQ ID NO 5
<211> LENGTH: 140
<212> TYPE: DNA
<213> ORGANISM: Artificial Sequence
<220> FEATURE:
<223> OTHER INFORMATION: Tetrahedron DNA construct

<400> SEQUENCE: 5
tacttccaat ccaattttt tttttcccat gagaataata ccgccgattt acgtcagtcc      60
ggttcccaca cgggacggca ggccgcacag aacacatacg cttgggcata gctgaacgcg    120
atatctcctg gtcgaatgcc                                                140

<210> SEQ ID NO 6
<211> LENGTH: 140
<212> TYPE: DNA
<213> ORGANISM: Artificial Sequence
<220> FEATURE:
<223> OTHER INFORMATION: Tetrahedron DNA construct

<400> SEQUENCE: 6
tacttccaat ccaattttt tttttgccca gattaaaacg tgaattccta gccagtacag      60
ggttccggac tgacgtaaat cggcggtatt attctcatgg gttggcacca cctgagtctc    120
gcccggctct tgtaagtcgg                                                140

<210> SEQ ID NO 7
<211> LENGTH: 135
<212> TYPE: DNA
<213> ORGANISM: Artificial Sequence
<220> FEATURE:
<223> OTHER INFORMATION: Tetrahedron DNA construct

<400> SEQUENCE: 7
tacttccaat ccaattttt ccctgtactg gctaggaatt cacgttttaa tctgggcttg      60
ggttaagaaa ctccccgcgc tggaggcgca tcaccgttgc gtatgtgttc tgtgcggcct    120
gccgtcccgt gtggg                                                     135

<210> SEQ ID NO 8
<211> LENGTH: 135
<212> TYPE: DNA
<213> ORGANISM: Artificial Sequence
<220> FEATURE:
<223> OTHER INFORMATION: Tetrahedron DNA construct
```

```
<400> SEQUENCE: 8
tacttccaat ccaattttt cggtgatgcg cctccagcgc ggggagtttc ttaacccttc      60
cgacttacaa gagccgggcg agactcaggt ggtgccttgg cattcgacca ggagatatcg    120
cgttcagcta tgccc                                                    135

<210> SEQ ID NO 9
<211> LENGTH: 135
<212> TYPE: DNA
<213> ORGANISM: Artificial Sequence
<220> FEATURE:
<223> OTHER INFORMATION: Tetrahedron DNA construct

<400> SEQUENCE: 9
tacttccaat ccaattttt cccatgagaa taataccgcc gatttacgtc agtccggttc     60
ccacacggga cggcaggccg cacagaacac atacgcttgg gcatagctga acgcgatatc   120
tcctggtcga atgcc                                                    135

<210> SEQ ID NO 10
<211> LENGTH: 135
<212> TYPE: DNA
<213> ORGANISM: Artificial Sequence
<220> FEATURE:
<223> OTHER INFORMATION: Tetrahedron DNA construct

<400> SEQUENCE: 10
tacttccaat ccaattttt gcccagatta aaacgtgaat tcctagccag tacagggttc     60
cggactgacg taaatcggcg gtattattct catgggttgg caccacctga gtctcgcccg   120
gctcttgtaa gtcgg                                                    135

<210> SEQ ID NO 11
<211> LENGTH: 132
<212> TYPE: DNA
<213> ORGANISM: Artificial Sequence
<220> FEATURE:
<223> OTHER INFORMATION: Tetrahedron DNA construct

<400> SEQUENCE: 11
ttccaatcca attttttccc tgtactggct aggaattcac gttttaatct gggcttgggt     60
taagaaactc cccgcgctgg aggcgcatca ccgttgcgta tgtgttctgt gcggcctgcc   120
gtcccgtgtg gg                                                       132

<210> SEQ ID NO 12
<211> LENGTH: 132
<212> TYPE: DNA
<213> ORGANISM: Artificial Sequence
<220> FEATURE:
<223> OTHER INFORMATION: Tetrahedron DNA construct

<400> SEQUENCE: 12
ttccaatcca attttttcgg tgatgcgcct ccagcgcggg gagtttctta accctttcga    60
cttacaagag ccgggcgaga ctcaggtggt gccttggcat tcgaccagga gatatcgcgt   120
tcagctatgc cc                                                       132

<210> SEQ ID NO 13
<211> LENGTH: 132
<212> TYPE: DNA
<213> ORGANISM: Artificial Sequence
<220> FEATURE:
<223> OTHER INFORMATION: Tetrahedron DNA construct
```

<400> SEQUENCE: 13
ttccaatcca attttttccc atgagaataa taccgccgat ttacgtcagt ccggttccca    60
cacgggacgg caggccgcac agaacacata cgcttgggca tagctgaacg cgatatctcc    120
tggtcgaatg cc    132

<210> SEQ ID NO 14
<211> LENGTH: 132
<212> TYPE: DNA
<213> ORGANISM: Artificial Sequence
<220> FEATURE:
<223> OTHER INFORMATION: Tetrahedron DNA construct

<400> SEQUENCE: 14
ttccaatcca attttttgcc cagattaaaa cgtgaattcc tagccagtac agggttccgg    60
actgacgtaa atcggcggta ttattctcat gggttggcac cacctgagtc tcgcccggct    120
cttgtaagtc gg    132

<210> SEQ ID NO 15
<211> LENGTH: 127
<212> TYPE: DNA
<213> ORGANISM: Artificial Sequence
<220> FEATURE:
<223> OTHER INFORMATION: Tetrahedron DNA construct

<400> SEQUENCE: 15
ccaatccaat ttccctgtac tggctaggaa ttcacgtttt aatctgggct tgggttaaga    60
aactccccgc gctggaggcg catcaccgtt gcgtatgtgt tctgtgcggc ctgccgtccc    120
gtgtggg    127

<210> SEQ ID NO 16
<211> LENGTH: 127
<212> TYPE: DNA
<213> ORGANISM: Artificial Sequence
<220> FEATURE:
<223> OTHER INFORMATION: Tetrahedron DNA construct

<400> SEQUENCE: 16
ccaatccaat ttcggtgatg cgcctccagc gcggggagtt tcttaaccct tccgacttac    60
aagagccggg cgagactcag gtggtgcctt ggcattcgac caggagatat cgcgttcagc    120
tatgccc    127

<210> SEQ ID NO 17
<211> LENGTH: 127
<212> TYPE: DNA
<213> ORGANISM: Artificial Sequence
<220> FEATURE:
<223> OTHER INFORMATION: Tetrahedron DNA construct

<400> SEQUENCE: 17
ccaatccaat ttcccatgag aataataccg ccgatttacg tcagtccggt tcccacacgg    60
gacggcaggc cgcacagaac acatacgctt gggcatagct gaacgcgata tctcctggtc    120
gaatgcc    127

<210> SEQ ID NO 18
<211> LENGTH: 127
<212> TYPE: DNA
<213> ORGANISM: Artificial Sequence
<220> FEATURE:

<223> OTHER INFORMATION: Tetrahedron DNA construct

<400> SEQUENCE: 18
ccaatccaat tgcccagat taaaacgtga attcctagcc agtacagggt tccggactga    60
cgtaaatcgg cggtattatt ctcatgggtt ggcaccacct gagtctcgcc cggctcttgt   120
aagtcgg                                                             127

<210> SEQ ID NO 19
<211> LENGTH: 125
<212> TYPE: DNA
<213> ORGANISM: Artificial Sequence
<220> FEATURE:
<223> OTHER INFORMATION: Tetrahedron DNA construct

<400> SEQUENCE: 19
aatccaattt ccctgtactg gctaggaatt cacgttttaa tctgggcttg ggttaagaaa    60
ctccccgcgc tggaggcgca tcaccgttgc gtatgtgttc tgtgcggcct gccgtcccgt   120
gtggg                                                               125

<210> SEQ ID NO 20
<211> LENGTH: 125
<212> TYPE: DNA
<213> ORGANISM: Artificial Sequence
<220> FEATURE:
<223> OTHER INFORMATION: Tetrahedron DNA construct

<400> SEQUENCE: 20
aatccaattt cggtgatgcg cctccagcgc ggggagtttc ttaacccttc cgacttacaa    60
gagccgggcg agactcaggt ggtgccttgg cattcgacca ggagatatcg cgttcagcta   120
tgccc                                                               125

<210> SEQ ID NO 21
<211> LENGTH: 125
<212> TYPE: DNA
<213> ORGANISM: Artificial Sequence
<220> FEATURE:
<223> OTHER INFORMATION: Tetrahedron DNA construct

<400> SEQUENCE: 21
aatccaattt cccatgagaa taataccgcc gatttacgtc agtccggttc ccacacggga    60
cggcaggccg cacagaacac atacgcttgg gcatagctga acgcgatatc tcctggtcga   120
atgcc                                                               125

<210> SEQ ID NO 22
<211> LENGTH: 125
<212> TYPE: DNA
<213> ORGANISM: Artificial Sequence
<220> FEATURE:
<223> OTHER INFORMATION: Tetrahedron DNA construct

<400> SEQUENCE: 22
aatccaattt gcccagatta aaacgtgaat tcctagccag tacagggttc cggactgacg    60
taaatcggcg gtattattct catgggttgg caccacctga gtctcgcccg gctcttgtaa   120
gtcgg                                                               125

<210> SEQ ID NO 23
<211> LENGTH: 126
<212> TYPE: DNA
<213> ORGANISM: Artificial Sequence

```
<220> FEATURE:
<223> OTHER INFORMATION: Tetrahedron DNA construct

<400> SEQUENCE: 23
ccaatccaat tccctgtact ggctaggaat tcacgtttta atctgggctt gggttaagaa    60
actccccgcg ctggaggcgc atcaccgttg cgtatgtgtt ctgtgcggcc tgccgtcccg   120
tgtggg                                                              126

<210> SEQ ID NO 24
<211> LENGTH: 126
<212> TYPE: DNA
<213> ORGANISM: Artificial Sequence
<220> FEATURE:
<223> OTHER INFORMATION: Tetrahedron DNA construct

<400> SEQUENCE: 24
ccaatccaat tcggtgatgc gcctccagcg cggggagttt cttaacccct tccgacttaca   60 agagccgggc gagactcagg tggtgccttg gcattcgacc aggagatatc gcgttcagct   120
atgccc                                                              126

<210> SEQ ID NO 25
<211> LENGTH: 126
<212> TYPE: DNA
<213> ORGANISM: Artificial Sequence
<220> FEATURE:
<223> OTHER INFORMATION: Tetrahedron DNA construct

<400> SEQUENCE: 25
ccaatccaat tcccatgaga ataataccgc cgatttacgt cagtccggtt cccacacggg    60
acggcaggcc gcacagaaca catacgcttg ggcatagctg aacgcgatat ctcctggtcg   120
aatgcc                                                              126

<210> SEQ ID NO 26
<211> LENGTH: 126
<212> TYPE: DNA
<213> ORGANISM: Artificial Sequence
<220> FEATURE:
<223> OTHER INFORMATION: Tetrahedron DNA construct

<400> SEQUENCE: 26
ccaatccaat tgcccagatt aaaacgtgaa ttcctagcca gtacagggtt ccggactgac    60
gtaaatcggc ggtattattc tcatgggttg gcaccacctg agtctcgccc ggctcttgta   120
agtcgg                                                              126

<210> SEQ ID NO 27
<211> LENGTH: 20
<212> TYPE: DNA
<213> ORGANISM: Artificial Sequence
<220> FEATURE:
<223> OTHER INFORMATION: Complementary sequences for particle
      functionalization

<400> SEQUENCE: 27
attggattgg aagtattttt                                                20

<210> SEQ ID NO 28
<211> LENGTH: 20
<212> TYPE: DNA
<213> ORGANISM: Artificial Sequence
```

```
<220> FEATURE:
<223> OTHER INFORMATION: Complementary sequences for particle
      functionalization

<400> SEQUENCE: 28
attggattgg tttttttttt                                                      20
```